United States Patent [19]

Widdig et al.

[11] Patent Number: 4,563,458

[45] Date of Patent: Jan. 7, 1986

[54] SUBSTITUTED 4-AMINOMETHYLENE-CHROMANS AND -CHROMENES, PROCESSES FOR THEIR PREPARATION AND THEIR USE IN MEDICAMENTS

[75] Inventors: Arno Widdig, Odenthal; Hans-Joachim Kabbe, Leverkusen; Andreas Knorr, Wuppertal; Ulrich Benz, Duesseldorf, all of Fed. Rep. of Germany

[73] Assignee: Bayer Aktiengesellschaft, Leverkusen, Fed. Rep. of Germany

[21] Appl. No.: 560,786

[22] Filed: Dec. 13, 1983

[30] Foreign Application Priority Data

Jan. 3, 1983 [DE] Fed. Rep. of Germany ....... 3300004

[51] Int. Cl.$^4$ .................. A61K 31/495; C07D 405/12
[52] U.S. Cl. ................................... 514/253; 514/450; 514/452; 514/457; 544/230; 544/376; 544/377; 549/330; 549/345; 549/350; 549/355; 549/383; 549/387; 549/389; 549/406; 549/407

[58] Field of Search ............... 544/376, 377, 250, 230; 549/330, 406, 407, 345, 350, 383, 387, 389; 260/330.9; 424/250; 514/253, 450, 452, 457

[56] References Cited

PUBLICATIONS

Zaugg, et al., "Chemical Abstracts", vol. 82, 1974, Col. 57517w.
"Chemical Abstracts", vol. 101; 1984, Col. 101: 191691n.
Widdig, et al., "Chemical Abstracts", vol. 102, 1984, Col. 102: 191691n.

Primary Examiner—Glennon H. Hollrah
Assistant Examiner—James H. Turnipseed
Attorney, Agent, or Firm—Sprung Horn Kramer & Woods

[57] ABSTRACT

The invention relates to substituted 4-aminomethylene-chromans and chromens of Formula (I) infra, as well as methods for making of said chromans and chromens, compositions containing said chromans and chromens and methods for the use of said chromans, chromens and compositions containing said chromans and chromens. The compounds and compositions of the invention are useful for their circulation influencing activity.

18 Claims, No Drawings

SUBSTITUTED 4-AMINOMETHYLENE-CHROMANS AND -CHROMENES, PROCESSES FOR THEIR PREPARATION AND THEIR USE IN MEDICAMENTS

The present invention relates to substituted 4-aminomethylene-chromans and -chromenes, a plurality of processes for their preparation and their use in medicaments, especially in agents which influence the circulation.

The novel compounds can be represented by the following formula (I):

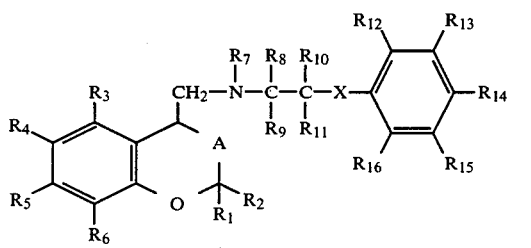

in which
—A— represents a single bond or a double bond, and
$R_1$ and $R_2$ are identical or different and represent hydrogen, alkyl, cycloalkyl, optionally substituted aryl or optionally substituted aralkyl
or in which
$R_1$ and $R_2$ together with the carbon atom which joins them form a carbocyclic ring,
$R_3$, $R_4$, $R_5$ and $R_6$ are identical or different and represent hydrogen, hydroxyl, halogen, alkyl, cycloalkyl, optionally substituted aryl, optionally substituted aralkyl, alkoxy, optionally substituted aryloxy and optionally substituted aralkoxy,
$R_7$, $R_8$, $R_9$, $R_{10}$ and $R_{11}$ are identical or different and represent hydrogen or alkyl,
X represents a single bond or methylene which is optionally substituted by one or two alkyl groups, or represents oxygen or $NR_{17}$
wherein
$R_{17}$ represents hydrogen or alkyl with up to 6 carbon atoms, or
$R_{17}$ together with $R_7$ can represent $C_2$-$C_3$-alkylene,
$R_{12}$, $R_{13}$, $R_{14}$, $R_{15}$ and $R_{16}$ are identical or different and represent hydrogen, hydroxyl, halogen, alkyl, cycloalkyl, optionally substituted aryl, optionally substituted aralkyl, alkoxy, aralkoxy, aryloxy or trifluoromethyl, and
$R_{12}$ and $R_{13}$ or
$R_{13}$ and $R_{14}$ can together represent an alkylenedioxy group or the —CH=CH—CH=CH— group
including their pharmaceutically acceptable acid addition salts.

Suitable alkyls in the substituents $R_1$-$R_{17}$ are straight-chain or branched $C_1$-$C_{18}$-alkyl radicals, preferably $C_1$-$C_{12}$-alkyl radicals, especially $C_1$-$C_6$-alkyl, more especially $C_1$-$C_3$-alkyl.

As examples of alkyl radicals there may be mentioned methyl, ethyl, propyl, isopropyl, butyl, isobutyl, tert.-butyl, hexyl, 2-hexyl, 1,1-dimethylpentyl, 1,1-dimethylhexyl, nonyl, decyl, undecyl and tetradecyl.

Suitable cycloalkyl radicals $R_1$, $R_2$, $R_3$, $R_4$, $R_5$, $R_6$ and $R_{12}$ to $R_{16}$ are preferably those with 3-18, more especially with 4-12, very especially with 5 and 6, carbon atoms, for example cyclopropyl, cyclobutyl, cyclopentyl, cyclohexyl, cycloheptyl, cyclooctyl, cyclododecyl, cycloheptadecyl and cyclooctadecyl, cyclopentyl and cyclohexyl being especially preferred.

Suitable optionally substituted aryl (more specifically mono- or bi-cyclic carbocyclic aryl) $R_1$, $R_2$, $R_3$ to $R_6$ and $R_{12}$ to to $R_{16}$ is aryl with, preferably, 6 to 10 carbon atoms in the aryl part. Examples which may be mentioned are optionally substituted phenyl, biphenyl naphthyl.

Suitable optionally substituted aralkyl radicals $R_1$, $R_2$, $R_3$ to $R_6$ and $R_{12}$ to $R_{16}$ are preferably those with 7 to 18 carbon atoms, whose aliphatic part contains 1 to 8, preferably 1 to 4, and particularly 1 to 2 carbon atoms, and whose aromatic part is a mono- or bi-cyclic carbocyclic radical with 6 to 10 carbon atoms. The following aralkyl radicals may be mentioned as examples: benzyl, phenylethyl, phenylpropyl, phenylbutyl and naphthylmethyl, benzyl being preferred.

Alkoxy $R_3$ to $R_6$ and $R_{12}$ to $R_{16}$ is straight-chain or branched alkoxy with preferably 1 to 6, especially 1 to 4, carbon atoms. Methoxy, ethoxy, n- and i-propoxy and n-, i- and t-butoxy may be mentioned as examples. As preferred aryloxy groups $R_3$ to $R_6$ and $R_{12}$ to $R_{16}$ there may be mentioned those mono- or bi-cyclic carbocyclic groups with 6 or 10 carbon atoms, such as phenoxy or naphthoxy.

As aralkoxy $R_3$ to $R_6$ and $R_{12}$ to $R_{16}$ there may be mentioned those mono- or bi-cyclic carbocyclic groups with, preferably, 7 to 10 carbon atoms, such as benzyloxy, phenylethoxy, phenylpropoxy, phenylisopropoxy, phenylbutoxy and phenylisobutoxy.

As halogens $R_3$ to $R_6$ and $R_{12}$ to $R_{16}$ there may be mentioned fluorine, chlorine, bromine and iodine, those preferred being fluorine, bromine and chlorine.

If the radicals $R_1$ and $R_2$ together with the carbon atom which joins them form a carbocyclic ring, then these may be 3- to 12-membered rings, preferably 4- to 7-membered rings. As examples of carbocyclic radicals there may be mentioned cyclopropane, cyclobutane, cyclopentane, cyclohexane, cycloheptane, cyclononane, cyclodecane and cyclododecane.

Suitable substituents of the aryl, aralkyl, aryloxy and aralkyloxy radicals $R_1$ to $R_6$ and $R_{12}$ to $R_{16}$ are substituents which do not undergo change under the reaction conditions. Examples which may be mentioned are the halogens, such as fluorine, chlorine, bromine and iodine, a $C_1$-$C_6$-alkyl group, a $C_1$-$C_6$-alkoxy group and the trifluoromethyl group.

As examples of acids for the preparation of the pharmaceutically acceptable acid-addition salts there may be mentioned sulphuric acid, hydrochloric acid, organic carboxylic acids, such as malic acid, citric acid, fumaric acid and acetic acid, or organic sulphonic acids, such as naphthalene-1,5-disulphonic acid.

These acid-addition salts of the compounds of the formula (I) can be obtained in a simple manner by conventional salt-forming methods, for example by dissolving the base and adding the acid, and can be isolated in a known manner, for example by filtering off, and be purified if desired.

Preferably, in formula (I):
$R_1$ and $R_2$ are identical or different and represent hydrogen, $C_1$-$C_6$-alkyl, $C_5$-$C_7$-cycloalkyl, phenyl which is optionally substituted (disubstituted or especially monosubstituted) by $C_1$-$C_4$-alkyl, halogen, (chlorine or bromine) and/or $C_1$-$C_4$-alkoxy, or $C_7$–$C_9$-aralkyl, whose aryl radical is optionally substituted (monosubstituted or disubstituted, especially monosubstituted) by $C_1$–$C_4$-alkyl, halogen (chlorine or bromine) and/or $C_1$–$C_4$-alkoxy, or $R_1$ and $R_2$ conjointly with the enclosed C atom of the chroman ring form a 4-membered to 7-membered carbocyclic ring;

$R_3$ to $R_6$ are identical or different and represent hydrogen, hydroxyl, halogen (chlorine or bromine), $C_1$–$C_6$-alkyl, $C_5$–$C_7$-cycloalkyl, phenyl which is optionally substituted (monosubstituted or disubstituted, especially monosubstituted) by $C_1$–$C_4$-alkyl, halogen (chlorine or bromine) and/or $C_1$–$C_4$-alkoxy, $C_7$–$C_9$-aralkyl, whose aryl radical is optionally substituted (monosubstituted or disubstituted, especially monosubstituted) by $C_1$–$C_4$-alkyl, halogen (chlorine or bromine) and/or $C_1$–$C_4$-alkoxy, or $C_1$–$C_4$-alkoxy, $R_7$, $R_8$, $R_9$, $R_{10}$ and $R_{11}$ are identical or different and represent hydrogen or $C_1$–$C_6$-alkyl, X represents a single bond or methylene which is optionally monosubstituted or disubstituted by $C_1$–$C_4$-alkyl, oxygen or —$NR_{17}$, wherein $R_{17}$ represents hydrogen or $C_1$–$C_4$-alkyl or $R_{17}$ together with $R_7$ can form a $C_2$-alkylene ring-closing member and $R_{12}$, $R_{14}$, $R_{15}$ and $R_{16}$ are identical or different and represent hydrogen, hydroxyl, halogen (chlorine, bromine or fluorine), $C_1$–$C_6$-alkyl, $C_5$- or $C_6$-cycloalkyl, benzyl, $C_1$–$C_4$-alkoxy, trifluoromethyl, and $R_{12}$ and $R_{13}$ or $R_{13}$ and $R_{14}$ together can form a $C_1$–$C_3$-alkylenedioxy group or a —CH=CH—CH=C— group.

Particularly preferred compounds of the formula (I) are those
in which $R_1$ and $R_2$, which may be identical or different, represent hydrogen or $C_1$–$C_4$-alkyl or together with the carbon atom which they enclose form a carbocyclic $C_5$- or $C_6$-ring, $R_3$ to $R_6$, which may be identical or different, denote hydrogen, hydroxyl, $C_1$–$C_4$-alkyl, $C_1$–$C_4$-alkoxy or chlorine, $R_7$ to $R_{11}$, which may be identical or different, represent hydrogen or $C_1$–$C_4$-alkyl, X represents a single bond, oxygen, methylene or —$NR_{17}$, wherein $R_{16}$ denotes hydrogen or $C_1$–$C_3$-alkyl or $R_{17}$ together with $R_7$ forms an ethylene ring-closing member and $R_{12}$ to $R_{16}$, which may be identical or different, denote hydrogen, chlorine, cyclohexyl, $C_1$–$C_4$-alkyl, $C_1$–$C_3$-alkoxy or trifluoromethyl, or $R_{12}$ and $R_{13}$ or $R_{13}$ and $R_{14}$ together form a methylenedioxy group or a —CH=CH—CH=CH— group.

As examples of novel compounds of the formula (I) which can, of course, be obtained by the procedure described generally herein as well as more specifically shown in the illustrative working examples, there may be mentioned: 4-β-phenylethylaminomethylchroman, 4-β-phenylethylaminomethyl-2,2-dimethylchroman, 4-β-phenylethylaminomethyl-2-isopropylchroman, 4-β-phenylethylaminoethyl-2-methyl-2-propyl-chroman, 4-β-phenylethylaminomethyl-2,2-diethylchroman, 4-β-phenylethylaminomethyl-2-spirocyclopentachroman, 4-β-phenylethylaminomethyl-2-spirocyclohexachroman, 4-β-phenylethylaminomethyl-2-hexylchroman, 4-β-phenylethylaminomethyl-2-cyclopentylchroman, 4-β-phenylethylaminomethyl-2-cyclohexylchroman, 4-β-phenylethylaminomethyl-2-phenylchroman, 4-β-phenylethylaminomethyl-2-benzylchroman, 4-β-phenylethylaminomethyl-2H-chromene, 4-β-phenylethylaminomethyl-2,2-dimethylchromene, 4-β-phenylethylaminomethyl-2-spirocyclopentachromene, 4-β-phenylethylaminomethyl-6-methyl-2-spirocyclopentachroman-4-β-phenylethylaminomethyl-7-methyl-2,2-dimethylchroman, 4-β-phenylethylaminomethyl-7-methyl-2-spirocyclopentachroman, 4-β-phenylethylaminomethyl-6-chloro-chroman, 4-β-phenylethylaminomethyl-6-chloro-2-spirocyclopentachroman, 4-β-phenylethylaminomethyl-6-methoxy-2,2-dimethylchroman, 4-β-phenylethylaminomethyl-6-methoxy-2-spirocyclopentachroman, 4-β-phenylethylaminomethyl-7-methoxy-2-spirocyclopentachroman, 4-β-phenylethylaminomethyl-7-phenyl-2-spirocyclopentachroman, 4-β-phenylethylaminomethyl-6,8-dichloro-2-spirocyclohexachroman, 4-β-phenylethylaminomethyl-5-hydroxy-2,2-dimethylchroman, 4-β-phenylethylaminomethyl-5-hydroxy-2-spirocyclopentachroman, 4-β-phenylethylaminomethyl-6-hydroxy-2-spirocyclopentachroman, 4-β-phenylethylaminomethyl-6-methyl-2-spirocyclohexachromene, 4-β-phenylethylaminomethyl-7-methyl-2,2-dimethylchromene, 4-β-phenylethylaminomethyl-6-chloro-2,2-dimethylchromene, 4-β-phenylethylaminomethyl-6-chloro-2-spirocyclopentachromene, 4-β-phenylethylaminomethyl-6-methoxy-2H-chromene, 4-β-phenylethylaminomethyl-6-methoxy-2-spirocyclopentachromene, 4-β-phenylethylaminomethyl-7-methoxy-2,2-dimethylchromene, 4-β-phenylethylaminomethyl-7-methoxy-2-isopropyl-2H-chromene, 4-β-phenylethylaminomethyl-7-phenyl-2-spirocyclopentachromene, 4-β-phenylethylaminomethyl-6,8-dichloro-2H-chromene, 4-β-phenylethylaminomethyl-5-hydroxy-2-spirocyclopentachromene, 4-β-(4-chlorophenyl)-ethylaminomethyl-2-spirocyclopentachroman, 4-β-(3,4-dichlorophenyl)-ethylaminomethyl-2,2-dimethylchroman, 4-β-(3-methylphenyl)-ethylaminomethyl-2-isopropylchroman, 4-β-(4-isopropylphenyl)-ethylaminomethyl-2,2-diethylchroman, 4-β-(3-methoxyphenyl)-ethylaminomethyl-2-spirocyclopentachroman, 4-β-(4-ethoxyphenyl)-ethylaminomethyl-2-spirocyclohexachroman, 4-β-(3,4-dimethoxyphenyl)-ethylaminomethyl-chroman, 4-β-(3,4-methylenedioxyphenyl)-ethylaminomethyl-2,2-dimethylchroman, 4-β-(3,4,5-trimethoxyphenyl)-ethylaminomethyl-2-methyl-2-isopropyl-chroman, 4-β-(4-hydroxyphenyl)-ethylaminomethyl-2,2-diethylchroman, 4-β-(4-trifluoromethylphenyl)-ethylaminomethyl-2-spirocyclopentachroman, 4-β-(3-chloro-4-trifluoromethylphenyl)-ethylaninomethyl-2-spirocyclohexachroman, 4-β-(1-naphthyl)-ethylaminomethyl-2b 2-spirocyclohexachroman, 4-β-(2-naphthyl)-ethylaminomethyl-2,2-dimethylchroman, 4-β-(4-chlorophenyl)-ethylaminomethyl-2-spirocyclohexachromene, 4-(β-phenyl-α-methylethyl)-aminomethyl-2-spirocyclohexachroman, 4-(β-phenyl-α,α-dimethylethyl)-aminomethyl-2,2-dimethylchroman, 4-(β-phenyl-α-ethylethyl)-aminomethyl-2-cyclopentylchroman, 4-(β-phenyl-3-methylethyl)-aminomethyl-2,2-diethylchroman, 4-(β-phenyl-α-methylethyl)-aminomethyl-2-spirocyclopentachromene, 4-γ-phenylpropylaminomethyl-2-spirocyclopentachroman, 4-γ-phenylpropylaminomethyl-2,2-dimethylchromene, 4-γ-phenylpropylaminomethyl-6- methyl-2,2-dimethylchroman, 4-γ-(3,4-methylenedioxyphenyl)-propylaminomethyl-2-spirocyclopentachroman, 4-[γ-(4-chlorophenyl)-α-methylpropyl]-aminomethyl-2-isopropyl-2H-chromene, 4-β-phenoxyethylaminomethyl-2,2-dimethylchroman, 4-β-phenoxyethylaminomethyl-2-spirocyclopentachroman, 4-β-phenoxyethylaminomethyl-2-spirocyclohexachroman, 4-β-phenoxyethylaminomethyl-2-spirocyclopentachromene, 4-β-phenoxyethylaminomethyl-6-methyl-2,2-dimethylchroman, 4-β-phenoxyethylaminomethyl-7-methyl-2-spirocyclopentachroman, 4-β-phenoxyethylaminomethyl-6-chloro-2-spirocyclohexachroman, 4-β-phenoxyethylaminomethyl-6-methoxychroman, 4-β-phenoxyethylaminomethyl-6-methoxy-2-phenylchroman, 4-β-phenoxyethylaminomethyl-7-methoxy-2-isopropylchroman, 4-β-phenoxyethylaminomethyl-7-phenyl-2,2-dimethylchroman, 4-β-phenoxyethylaminomethyl-6,8-dichloro-2-spirocyclohexachroman, 4-β-phenoxyethylaminomethyl-6,8-dimethyl-2-hexylchroman, 4-β-phenoxyethylaminomethyl-5-hydroxychroman, 4-β-phenoxyethylaminomethyl-6-hydroxy-2-spirocyclopentachroman, 4-β-phenoxyethylaminomethyl-6-methyl-2,2-dimethylchromene, 4-β-(4-chlorophenoxy)-ethylaminomethylchroman, 4-β-(3,4-dichlorophenoxy)-ethylaminomethyl-2,2-dimethylchroman, 4-β-(3-methylphenoxy)-ethylaminomethyl-2-methyl-2-isopropylchroman, 4-β-(4-isopropylphenoxy)-ethylaminomethyl-2,2-diethylchroman, 4-β-(4-ethoxyphenoxy)-ethylaminomethyl-2-spirocyclohexachroman, 4-β-(3,4-dimethoxyphenoxy)-ethylaminomethyl-2-spirocyclopentachroman, 4-β-(3,4-methylenedioxyphenoxy)-ethylaminomethyl-2,2-dimethylchroman, 4-β-(3,4,5-trimethoxyphenoxy)-ethylaminomethyl-2-cyclopentylchroman, 4-β-(4-hydroxyphenoxy)-ethylaminomethyl-2,2-diethylchroman, 4-β-(4-chlorophenoxy)-ethylaminomethyl-2H-chromene, 4-(β-phenoxy-α-methylethyl)-aminomethyl-2-spirocyclohexachroman, 4-(β-phenoxy-β-methylethyl)-aminomethyl-2,2-diethylchroman, 4-(β-phenoxy-α-methylethyl)-aminomethyl-2-spirocyclopentachromene, 4-(γ-phenyl-α-methylpropyl)-aminomethyl-2H-chromene, 4-(γ-phenyl-α-methylpropyl)-aminomethyl-2-spirocyclopentachromene, 4-(γ-phenyl-α-methylpropyl)-aminomethyl-2,2-dimethylchroman, 4-(γ-phenyl-α-methylpropyl)-aminomethyl-2-spirocyclopentachroman, 4-(γ-phenyl-α-methylpropyl)-aminomethyl-6-methyl-2,2-dimethylchroman, 4-(γ-phenyl-α-methylpropyl)-aminomethyl-6-chloro-2-spirocyclohexachroman, 4-(γ-phenyl-α-methylpropyl)-aminomethyl-7-methoxy-2-benzylchroman, 4-(γ-phenyl-α-methylpropyl)-aminomethyl-7-phenyl-2-cyclopentylchroman, 4-(γ-phenyl-α-methylpropyl)-aminomethyl-6,8-dichlorochroman, 4-(γ-phenyl-α-methylpropyl)-aminomethyl-6,8-dimethyl-2-cyclohexylchroman, 4-(γ-phenyl-α-methylpropyl)-aminomethyl-5-hydroxy-2-spirocyclopentachroman, 4-(γ-phenyl-α-methylpropyl)-aminomethyl-6-hydroxychroman, 4-(γ-3,4-methylenedioxyphenyl-α-methylpropyl)-aminomethylchroman, 4-(γ-3,4-methylenedioxyphenyl-α-methylpropyl)-aminomethyl-2,2-dimethylchroman, 4-(γ-3,4-methylenedioxyphenyl-α-methylpropyl)-aminomethyl-2-isopropylchroman, 4-(γ-3,4-methylenedioxyphenyl-α-methylpropyl)-aminomethyl-2,2-diethylchroman, 4-(γ-3,4-methylenedioxyphenyl-α-methylpropyl)-aminomethyl-2-spirocyclopentachroman, 4-(γ-3,4-methylenedioxyphenyl-α-methylpropyl)-aminomethyl-2-spirocyclohexachroman, 4-(γ-3,4-methylenedioxyphenyl-α-methylpropyl)-aminomethyl-7-methyl-2-spirocyclopentachroman, 4-(γ-3,4-methylenedioxyphenyl-α-methylpropyl)-aminomethyl-6-chloro-2-spirocyclopentachroman, 4-(γ-3,4-methylenedioxyphenyl-α-methylpropyl)-aminomethyl-6-methoxy-2-spirocyclopentachroman, 4-(γ-3,4-methylenedioxyphenyl-α-methylpropyl)-aminomethyl-7-methoxy-2-spirocyclopentachroman, 4-(γ-3,4-methylenedioxyphenyl-α-methylpropyl)-aminomethyl-7-phenyl-2-spirocyclopentachroman, 4-(γ-3,4-methylenedioxyphenyl-α-methylpropyl)-aminomethyl-2,2-dimethylchromene, 4-(γ-3,4-methylenedioxyphenyl-α-methylpropyl)-aminomethyl-2-spirocyclopentachromene, 4-(γ-3-trifluoromethylphenyl-α-methylpropyl)-aminomethyl-2-spirocyclopentachroman, 4-(γ-3,4-dimethoxyphenyl-α-methylpropyl)-aminomethyl-2-spirocyclopentachroman, 4-(γ-2,4-dimethoxyphenyl-α-methylpropyl)-aminomethyl-2-spirocyclopentachroman, 4-(γ-4-chlorophenyl-α-methylpropyl)-aminomethyl-2-spirocyclopentachroman, 4-(γ-3,4,5-trimethoxyphenyl-α-methylpropyl)-aminomethyl-2-spirocyclopentachroman, 4-(γ-3,4-dimethoxyphenyl-α-methylpropyl)-aminomethyl-2-spirocyclopentachromene, 4-(γ-chlorophenyl-α-methylpropyl)-aminomethyl-2-spirocyclopentachromen, 4-β-phenylaminoethylaminomethyl-2,2-dimethylchroman, 4-β-phenylaminoethylaminomethyl-2-spirocyclopentachroman, 4-β-phenylaminoethylaminomethyl-2-spirocyclopentachromene, 4-β-(4-chlorophenyl)-aminoethylaminomethyl-2-spirocyclohexachroman, 4-β-(3,4-dichlrophenyl)-aminoethylaminomethyl-2,2-dimethylchroman, 4-β-(4-isopropylphenyl)-aminoethylaminomethyl-2-cyclohexylchroman, 4-β-(4-ethoxyphenyl)-aminoethylaminomethyl-2-spirocyclohexachroman, 4-(N-phenylpiperazin-N'-ylmethyl)-2,2-dimethylchroman, 4-(N-phenylpiperazin-N'-yl-methyl)-2-spirocyclopentachroman, 4-(N-phenylpiperazin-N'-ylmethyl)-2-spirocyclohexachroman, 4-(N-phenylpiperazin-N'-ylmethyl)-7-methyl-2,2-dimethylchroman, 4-(N-phenylpiperazin-N'-ylmethyl)-6-chloro-2-spirocyclopentachroman, 4-(N-phenylpiperazin-N'-ylmethyl)-6-methoxy-2-spirocyclohexachroman, 4-(N-phenylpiperazin-N'-ylmethyl)-7-methoxy-2,2-diethylchroman, 4-N-(4-chlorophenyl)-piperazin-N'-ylmethyl-2-spirocyclohexachroman, 4-N-(3,4-dichlorophenyl)-piperazin-N'-ylmethyl-2,2-dimethylchroman, 4-N-(3,4-dichlorophenyl)-piperazin-N'-ylmethyl-2b 2-hexylchroman, 4-N-(3,4-dimethoxyphenyl)-piperazin-N'-ylmethyl-2-spirocyclopentachroman, 4-N-(3,4-methylenedioxyphenyl)-piperazin-N'-ylmethyl-2,2-dimethylchroman, 4-N-(3,4,5-trimethoxyphenyl)-piperazin-N'-ylmethyl-2-methyl-2-propylchroman, 4-(N-phenylpiperazin-N'-ylmethyl)-2H-chromene, 4-(N-phenylpiperazin-N'-ylmethyl)-2,2-dimethylchromene, 4-(N-phenylpiperazin-N'-methyl)-6-methyl-2,2-dimethylchromene, 4-(N-phenylpiperazin-N'-ylmethyl)-6-chloro-2-spirocyclopentachromene, 4-(N-phenylpiperazin-N'-ylmethyl)-6-methoxy-2-spirocyclohexachromene, 4-(N-phenylpiperazin-N'-ylmethyl)-7-methoxy-2,2-diethylchromene, 4-(N-phenylpiperazin-N'-ylmethyl)-7-phenyl-2-benzyl-2H-chromene, 4-(N-phenylpiperazin-N'-ylmethyl)-5-hydroxy-2,2-dimethylchromene, 4-N-(4-chlorophenyl)-piperazin-N'-ylmethyl-2-spirocyclopentachromene, 4-N-(3,4-dichlorophenyl)-piperazin-N'-ylmethyl-2,2-dimethylchromene, 4-N-(3-methylphenyl)-piperazin-N'-ylmethyl-2-methyl-2-propylchromene, 4-N-(4-isopropylphenyl)-piperazin-N'-ylmethyl-2,2-diethylamylchromene, 4-N-(3-methoxyphenyl)-piperazin-N'-ylmethyl-2-spirocyclopentachromene, 4-N-(4-ethoxyphenyl)-piperazin-N'-ylmethyl-2-spirocyclohexachromene, 4-N-(3,4-dimethoxyphenyl)-piperazin-N'-ylmethyl-2H-chromene, 4-N-(3,4-methylenedioxyphenyl)-piperazin-N'-ylmethyl-2,2-dimethylchromene, 4-N-(3,4,5-trimethoxyphenyl)-piperazin-N'-ylmethyl-2-isopropyl-2H-chromene, 4-N-(4-hydroxyphenyl)-piperazin-N'-ylmethyl-2,2-diethylchromene, 4-N-(trifluoromethylphenyl)-piperazin-N-ylmethyl-2-spirocyclopentachromene and 4-N-(3-chloro-4-trifluoromethyl)-piperazin-N-ylmethyl-2-spirocyclohexachromene.

The following compounds may be mentioned especially: 4-[γ-(3,4-methylenedioxyphenyl)-α-methylpropyl]-aminomethyl-2-spirocyclopentachroman, 4-(β-phenylethyl)-aminomethyl-2-spirocyclopentachroman, 4-N-3,4-dichlorophenyl-piperazin-N'-ylmethyl-2,2-dimethylchromene, 4-β-phenoxyethyl-aminomethyl-2-spirocyclopentachroman, 4-[γ-(3,4,5-trimethoxyphenyl)-α-methylpropyl]-2-spirocyclopentachroman and 4-[γ-(3-trifluoromethylphenyl)-α-methylpropyl]-2-spirocyclopentachroman.

The invention moreover relates to various processes for the preparation of the compounds of the formula (I).
Either
(A) chroman-4-carbaldehydes of the formula (II)

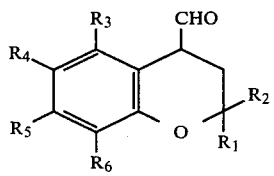

in which
R$_1$, R$_2$, R$_3$, R$_4$, R$_5$ and R$_6$ have the above-mentioned meaning
are reacted with amines of the formula (III)

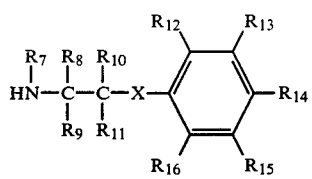

in which
R$_7$, R$_8$, R$_9$, R$_{10}$, R$_{11}$, R$_{12}$, R$_{13}$, R$_{14}$, R$_{15}$, R$_{16}$, R$_{17}$ and X have the abovementioned meaning
in the presence of reducing agents, or
(B) amines of the formula (IV)

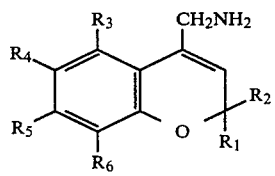

or of the formula (V)

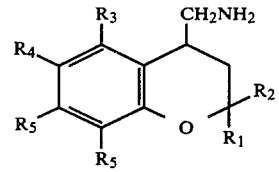

in which
R$_1$, R$_2$, R$_3$, R$_4$, R$_5$ and R$_6$ have the abovementioned meaning
are reacted with carbonyl compounds of the formula (VI)

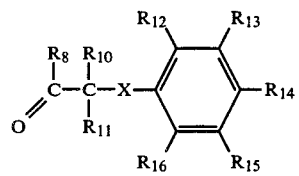

in which
R$_8$ to R$_{16}$ have the abovementioned meaning, with the proviso that X does not represent NR$_{17}$, in the presence of reducing agents, or
(C) halides of the formula (VII)

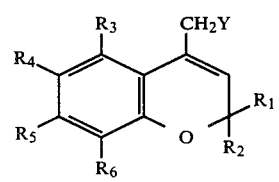

in which
R$_1$, R$_2$, R$_3$, R$_4$, R$_5$ and R$_6$ have the abovementioned meaning and
Y represents bromine or chlorine,
are reacted with the amines of the formula (III) in the presence of an acid-binding agent.

Complex metal hydrides are examples of reducing agents which can be employed in process variants A and B. Alkali metal borohydrides, alkali metal cyanoborohydrides and/or alkali metal alanates, especially sodium compounds or lithium compounds, are preferred, more specifically, sodium borohydride, sodium cyanoborohydride or lithium alanate. One can also employ catalytically activated hydrogen at elevated pressures and temperatures.

The reducing agents can be employed in quantities ranging from equivalent amounts to an excess of 100%, preferably equivalent amounts to an excess of 20%, relative to the carbonyl compound employed.

The acid-binding agents employed in preparation variant C are known bases. Examples which may be mentioned are alkaline earth metal hydroxides or alkali metal hydroxides, such as sodium hydroxide and/or potassium hydroxide, alkaline earth metal carbonates or alkali metal carbonates such as sodium bicarbonate or potassium carbonate, and organic nitrogen bases such as triethylamine, tributylamine or quaternary ammonium bases, such as benzyltrimethylammonium hydroxide.

These acid-binding agents can be employed in quantities ranging from equivalent amounts to an excess of 100%, preferably from equivalent amounts to an excess of 20%, relative to the halogen compound employed.

The reactions according to the invention are carried out in solvents. Suitable solvents are all those which are inert to the particular reaction; the following are mentioned as being preferred; alcohols such as methanol, ethanol, isopropanol or tert.-butanol, ethers (particularly $C_1$–$C_3$-dialkyl ethers) such as diethyl ether, diisopropyl ether, tetrahydrofuran or dioxane, hydrocarbons such as hexane, cyclohexane, benzene or toluene, chlorohydrocarbons such as methylene chloride, chloroform, carbon tetrachloride or chlorobenzene, or mixtures of such solvents.

The reaction temperatures can be varied over a substantial range. In general, the reaction is carried out between −50° and 150° C., preferably −10° to 120° C.

In carrying out the process according to the invention it is preferred to react 0.5 to 2 mol of the amine of the formula (III) or of the carbonyl compound of the formula (VI) per mol of the chroman or chromene compound. A molar ratio of the reactants of 1:1 is particularly preferred. If an excess is used, then it is preferred to employ an excess of amine of the formula (III) or of carbonyl compound of the formula (VI).

The reaction products can be isolated by distillation, crystallising-out, concentration and recrystallisation or chromatographic separation.

The chroman-4-aldehydes of the formula (II) are prepared from 2H-chromenes by hydroformylation in accordance with the following equation:

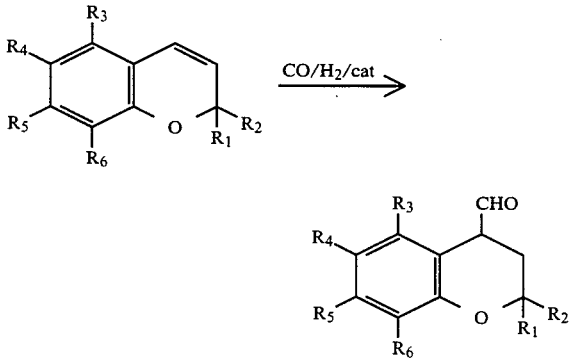

wherein $R_1$, $R_2$, $R_3$, $R_4$, $R_5$ and $R_6$ are defined as above.

The process is characterised in that the 2H-chromenes are reacted with carbon monoxide and hydrogen in the presence of metal catalysts of sub-group 8 of the periodic table, at temperatures of 80° to 250° C. and pressures of 20–1,000 bar.

Examples of the chroman-4-carbaldehydes are: 4-formylchroman, 4-formyl-2-methylchroman, 4-formyl-2,2-dimethylchroman, 4-formyl-2-propylchroman, 4-formyl-2-isopropylchroman, 4-formyl-2,2-diethylchroman, 4-formyl-2-methyl-2-propylchroman, 4-formyl-2-hexylchroman, 4-formyl-2-cyclopentylchroman, 4-formyl-2-cyclohexylchroman, 4-formyl-2-spirocyclopentachroman, 4-formyl-2-spirocyclohexachroman, 4-formyl-6-methyl-2-spirocyclopentachroman, 4-formyl-7-methyl-2-spirocyclopentachroman, 4-formyl-6,8-dimethyl-2-spirocyclopentachroman, 4-formyl-6-chloro-2-spirocyclopentachroman, 4-formyl-6-methoxy-2-spirocyclopentachroman, 4-formyl-7-methoxy-2-spirocyclopentachroman, 4-formyl-7-isopropoxy-2-spirocyclopentachroman, 4-formyl-7-phenoxy-2-spirocyclopentachroman, 4-formyl-7-benzyloxy-2-spirocyclopentachroman, 4-formyl-7-phenyl-2-spirocyclopentachroman, 4-formyl-6-methyl-2,2-dimethylchroman, 4-formyl-6-chloro-2,2-dimethylchroman, 4-formyl-7-methoxy-2,2-dimethylchroman, 4-formyl-6-methyl-2-spirocyclohexachroman and 4-formyl-7-methoxy-2-spirocyclohexachroman.

A large proportion of the amines of the formula (III) employed in the preparation of the compounds according to the invention is known (compare, for example, Beilsteins Handbuch der organischen Chemie (Beilstein's Handbook of Organic Chemistry) 6, 172, III 639, IV 663; 12; 543, 1096, 1145, I 473, 494, II 287, 591, 623, III/IV 49); those not previously known can be obtained by analogous methods.

As examples of the amines of the formula (III) there may be mentioned: 2-phenylethylamine, 2-(2-chlorophenyl)ethylamine, 2-(4-chlorophenyl)-ethylamine, 2-(3,4-dichlorophenyl)-ethylamine, 2-(3-methylphenyl)-ethylamine, 2-(2,4-dimethylphenyl)-ethylamine, 2-(2-methyl-4-chlorophenyl)-ethylamine, 2-(4-hydroxyphenyl)-ethylamine, 2-(4-methoxyphenyl)-ethylamine, 2-(3,4-dimethoxyphenyl)-ethylamine, 2-(α-naphthyl)-ethylamine, 2-(β-naphthyl)-ethylamine, 2-(3,4-methylenedioxyphenyl)-ethylamine, 3-phenyl-propylamine, 2-phenylpropylamine, 3-(4-chlorophenyl)-propylamine, 2-(4-chlorophenyl)-propylamine, 3-(4-methylphenyl)-propylamine, 2-(3-methylphenyl)-propylamine, 3-(4-methoxyphenyl)-propylamine, 2-(3,4-dimethoxyphenyl)-propylamine, 3-(3,4-methylenedioxyphenyl)-propylamine, 2-amino-4-phenyl-butane, 2-amino-4-(4-chlorophenyl)-butane, 2-amino-4-(4-methylphenyl)-butane, 2-amino-4-(4-trifluoromethylphenyl)-butane, 2-amino-4-(4-isopropylphenyl)-butane, 2-amino-4-(3,4-dichlorophenyl)-butane, 2-amino-4-(2-methoxyphenyl)-butane, 2-amino-4-(3-methoxyphenyl)-butane, 2-amino-4-(4-methoxyphenyl)-butane, 2-amino-4-(4-propoxyphenyl)-butane, 2-amino-4-(3,4-dimethoxyphenyl)-butane, 2-amino-4-(3,4-methylenedioxyphenyl)-butane, 3-amino-5-phenylpentane, 3-amino-5-(3,4-methylenedioxyphenyl)-pentane, 2-phenyl-1-methyl-ethylamine, 2-phenyl-1,1-dimethylethylamine, 2-phenyl-1,1-diethyl-ethylamine, 2-phenyl-2,2-dimethyl-ethylamine, 2-phenyl-2,2-diethyl-ethylamine, 2-phenyl-N-methyl-ethylamine, 2-phenyl-N-ethyl-ethylamine, 2-phenyl-N-isopropyl-ethylamine, 2-(4-chlorophenyl)-N-methyl-ethylamine, 2-(4-methoxyphenyl)-N-methyl-ethylamine, 2-(4-isopropylphenyl)-N-methyl-ethylamine, 2-phenoxyethylamine, 2-(4-methylphenoxy)-ethylamine, 2-(4-tert.-butylphenoxy)-ethylamine, 2-(4-chlorophenoxy)-ethylamine, 2-(4-trifluoromethylphenoxy)-ethylamine, 2-(3-ethoxyphenoxy)-ethylamine, 2-(4-methoxyphenoxy)-ethylamine, 2-(4-isopropoxyphenoxy)-ethylamine, 2-phenoxypropylamine, 2-(4-fluorophenoxy)-propylamine, 2-phenoxybutaneamine, 2-phenoxy-N-methyl-ethylamine, 2-phenoxy-N-ethyl-ethylamine, 2-phenoxy-N-isopropyl-ethylamine, N-phenyl-ethylenediamine, N-(4-chlorophenyl)-ethylenediamine, N-(3,4-dichlorophenyl)-ethylenediamine, N-(4-methylphenyl)-ethylenediamine, N-(4-isopropylphenyl)-ethylenediamine, N-(4-trifluoromethylphenyl)-ethylenediamine, N-(4-hydroxyphenyl)-ethylenediamine, N-(2-methoxyphenyl)-ethylenediamine, N-(4-ethoxyphenyl)-ethylenediamine, N-phenyl-N'-methyl-ethylenediamine, N-phenyl-N'-ethyl-ethylenediamine, N-(4-chlorophenyl)-N'-isopropylethylenediamine, N-phenyl-N-methyl-ethylenediamine, 2-amino-3-anilino-propane, 3-amino- 4-anilino-butane, 2-amino-2-methyl-3-anilino-propane, 2-amino-2-methyl-3-(4-chloroanilino)-propane, 1-amino-2-anilino-propane, 1-amino-2-anilino-butane, 1-amino-2-methyl-2-anilino-propane, 1-amino-2-methyl-2-(4-methoxyanilino)-propane, N-phenylpiperazine, N-(2-chlorophenyl)-piperazine, N-(4-chlorophenyl)-piperazine, N-(3,4-dichlorophenyl)-piperazine, N-(4-trifluoromethylphenyl)-piperazine, N-(3-trifluoromethylphenyl)-piperazine, N-(3-trifluoromethyl-4-chlorophenyl)-piperazine, N-(2-methoxyphenyl)-piperazine, N-(2-ethoxyphenyl)-piperazine, N-(2-isopropoxyphenyl)-piperazine, N-(3-methoxyphenyl)-piperazine, N-(4-methoxyphenyl)-piperazine, N-(3,4-dimethoxyphenyl)-piperazine, N-(3,4-methylenedioxyphenyl)-piperazine, N-(4-methylphenyl)-piperazine, N-(3,4-dimethylphenyl)-piperazine, N-(2,4-dimethylphenyl)-piperazine, N-(2,5-dimethylphenyl)-piperazine, N-(4-ethylphenyl)-piperazine, N-(4-isopropylphenyl)-piperazine, N-(4-tert.-butylphenyl)-piperazine and N-(4-cyclohexylphenyl)-piperazine.

Some of the amines of the formula (IV) employed in the preparation of the compounds according to the invention are known (J. med. Chem. 1982, 393). Those not previously known can be prepared by analogous methods.

In doing so, the starting materials are chroman-4-ones which are reacted with trimethylsilyl cyanide, as indicated in the following equation:

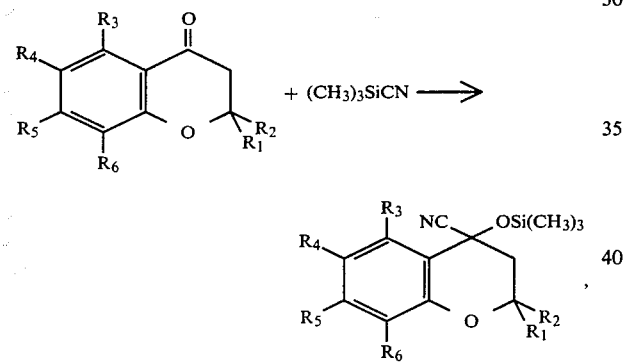

wherein $R_1$, $R_2$, $R_3$, $R_4$, $R_5$ and $R_6$ are defined as above.

The 4-cyano-4-trimethylsilyloxychromans thus produced can be hydrogenated by means of lithium aluminium hydride to give 4-aminomethyl-4-hydroxychromans, as indicated in the following equation:

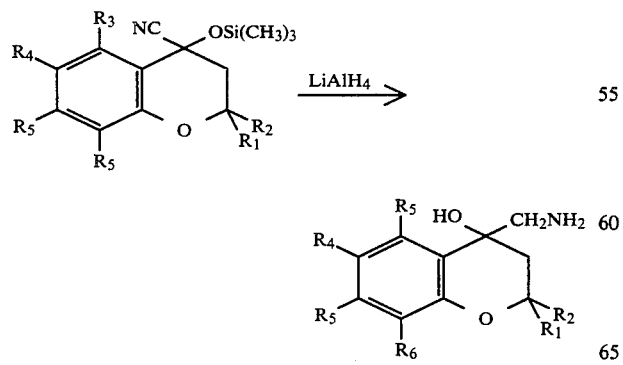

The 4-aminomethyl-4-hydroxychromans can be converted by dehydrating agents into the 4-aminomethyl-2H-chromenes of the formula (IV) as shown in the equation below.

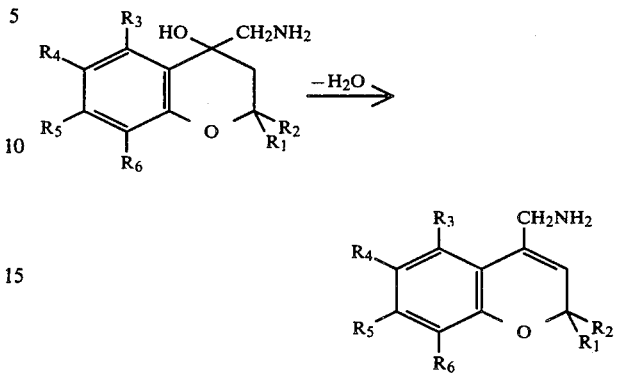

The aminomethylchromenes can be converted to the aminomethylchromans by hydrogenation, as in the following equation:

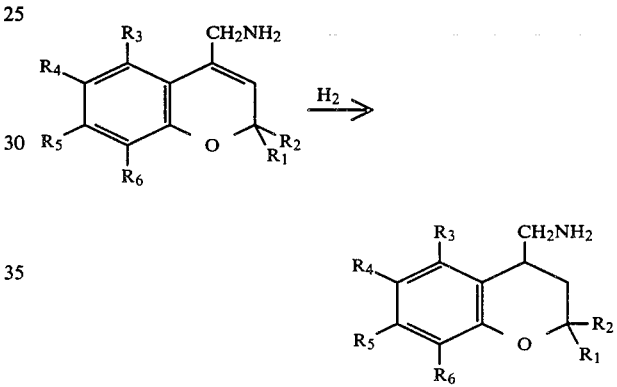

It is however, also possible to eliminate trimethylsilanol from the 4-cyano-4-trimethylsilyloxychromans by means of phosphorus oxychloride and thus isolate 4-cyano-2H-chromenes, as indicated in the following equation (analogously to a method from Chemistry Letters 1979, 1427):

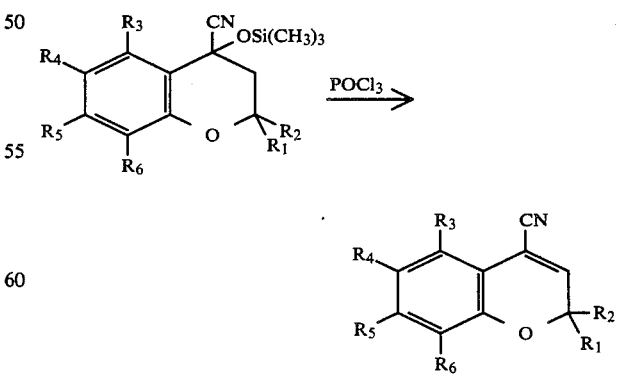

The 4-cyano-2H-chromenes can then be hydrogenated directly or stepwise to give the 4-aminomethylchromans, as represented in the following equation:

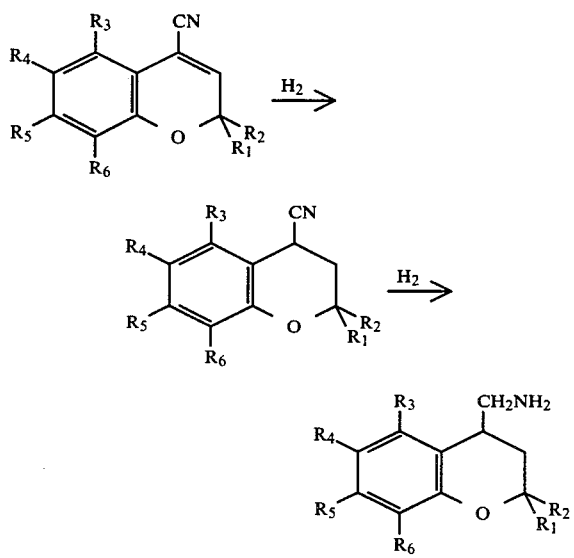

As examples of the 4-aminomethyl-2H-chromenes there may be mentioned: 4-aminomethyl-2H-chromene, 4-aminomethyl-2-methyl-2H-chromene, 4-aminomethyl-2,2-dimethyl-chromene, 4-aminomethyl-2-propyl-2H-chromene, 4-aminomethyl-2-isopropyl-2H-chromene, 4-aminomethyl-2,2-diethyl-chromene, 4-aminomethyl-2-methyl-2-propyl-chromene, 4-aminomethyl-2-hexyl-2H-chromene, 4-aminomethyl-2-cyclopentyl-2H-chromene, 4-aminomethyl-2-cyclohexyl-2H-chromene, 4-aminomethyl-2-spirocyclopentachromene, 4-aminomethyl-2-spirocyclohexachromene, 4-aminomethyl-6-methyl-2-spirocyclopentachromene, 4-aminomethyl-7-methyl-2-spirocyclopentachromene, 4-aminomethyl-6,8-dimethyl-2-spirocyclopentachromene, 4-aminomethyl-6-chloro-2-spirocyclopentachromene, 4-aminomethyl-6-methoxy-2-spirocyclopentachromene, 4-aminomethyl-7-methoxy-2-spirocyclopentachromene, 4-aminomethyl-7-isopropoxy-2-spirocyclopentachromene, 4-aminomethyl-7-phenoxy-2-spirocyclopentachromene, 4-aminomethyl-7-benzyloxy-2-spirocyclopentachromene, 4-aminomethyl-7-phenyl-2-spirocyclopentachromene, 4-aminomethyl-6-methyl-2-spirocyclohexachromene, 4-aminomethyl-6-chloro-2-spirocyclohexachromene, 4-aminomethyl-7-methoxy-2-spirocyclohexachromene, 4-aminomethyl-6-methyl-2,2-dimethylchromene and 4-aminomethyl-7-methoxy-2,2-dimethylchromene.

Some of the amines of the formula (V) employed in the preparation of the compounds according to the invention are known (J. med. Chem. 1982, 393). Those not previously known can be obtained by analogous methods, for example as described above.

As examples of the 4-aminomethylchromans there may be mentioned: 4-aminomethyl-chroman, 4-aminomethyl-2-methyl-chroman, 4-aminomethyl-2,2-dimethyl-chroman, 4-aminomethyl-2-propyl-chroman, 2-aminomethyl-2-isopropyl-chroman, 4-aminomethyl-2,2-diethyl-chroman, 4-aminomethyl-2-methyl-4-propyl-chroman, 4-aminomethyl-2-hexyl-chroman, 4-aminomethyl-2-cyclopentyl-chroman, 4-aminomethyl-2-cyclohexyl-chroman, 4-aminomethyl-2-spirocyclopenta-chroman, 4-aminomethyl-2-spirocyclohexa-chroman, 4-aminomethyl-6-methyl-2-spirocyclopenta-chroman, 4-aminomethyl-7-methyl-2-spirocyclopenta-chroman, 4-aminomethyl-6,8-dimethyl-2-spirocyclopenta-chroman, 4-aminomethyl-6-chloro-2-spirocyclopenta-chroman, 4-aminomethyl-6-methoxy-2-spirocyclopenta-chroman, 4-aminomethyl-7-methoxy-2-spirocyclopenta-chroman, 4-aminomethyl-8-isopropoxy-2-spirocyclopenta-chroman, 4-aminomethyl-7-phenoxy-2-spirocyclopenta-chroman, 4-aminomethyl-7-benzyloxy-2-spirocyclopenta-chroman, 4-aminomethyl-7-phenyl-2-spirocyclopenta-chroman, 4-aminomethyl-6-methyl-2-spirocyclohexachroman, 4-aminomethyl-6-chloro-2-spirocyclohexachroman, 4-aminomethyl-7-methoxy-2-spirocyclohexachroman, 4-aminomethyl-6-methyl-2,2-dimethylchroman and 4-aminomethyl-7-methoxy-2,2-dimethylchroman.

A high proportion of the carbonyl compounds of the formula (VI) used in the preparation of the process according to the invention are known (compare, for example, Beilsteins Handbuch der organischen Chemie (Beilstein's Handbook of Organic Chemistry) 6, 151, II 152; 7, 292, 303, 304, 314, I 154, 161, 162, 167, II 226, 233, 236, 243). Those not previously known can be prepared by analogous methods.

As examples of the carbonyl compounds there may be mentioned: phenylacetaldehyde, 2-chlorophenylacetaldehyde, 3-chlorophenylacetaldehyde, 4-chlorophenylacetaldehyde, 3,4-dichlorophenylacetaldehyde, 4-methylphenylacetaldehyde, 4-isopropylphenylacetaldehyde, 3-methoxyphenylacetaldehyde, 4-ethoxyphenylacetaldehyde, 3,4-dimethoxyphenylacetaldehyde, 3,4-methylenedioxyphenylacetaldehyde, α-phenylpropionaldehyde, β-phenylpropionaldehyde, β-(4-chlorophenyl)-propionaldehyde, α-(4-trifluoromethylphenyl)-propionaldehyde, β-(4-trifluoromethylphenyl)-propionaldehyde, β-(4-methoxyphenyl)-propionaldehyde, β-(3,4-dimethoxyphenyl)-propionaldehyde, β-(3,4-methylenedioxyphenyl-propionaldehyde, phenoxyacetaldehyde, 4-chlorophenoxyacetaldehyde, 3,4-dichloro-phenoxyacetaldehyde, 2,4-dichlorophenoxyacetaldehyde, 3,4-dimethylphenoxyacetaldehyde, 4-methoxyphenoxyacetaldehyde, 3,4-dimethoxyphenoxyacetaldehyde, 3,4-methylenedioxyphenylacetaldehyde, phenylacetone, 4-chlorophenylacetone, 3,4-dichlorophenylacetone, 4-methylphenylacetone, 4-methoxyphenylacetone, 3,4-dimethoxyphenylacetone, 3,4-methylenedioxyphenylacetone, benzylacetone, (4-chlorobenzyl)-acetone, (4-trifluoromethylbenzyl)-acetone, (4-methoxybenzyl)-acetone, (3,4-dimethoxybenzyl)-acetone, (3,4-methylenedioxybenzyl)-acetone, phenoxyacetone, (4-chlorophenoxy)-acetone, (3,4-dichlorophenoxy)-acetone, (2,5-dimethylphenoxy)-acetone, (4-methoxyphenoxy)-acetone, (3,4-dimethoxyphenoxy)-acetone and (3,4-methylenedioxyphenoxy)-acetone.

Some of the halides of the formula (VII) employed in the preparation of the compounds according to the invention are known (Tetrahedron 23, 1893 (1967)). Those not previously known can be prepared by an analogous method or from 4-methyl-2H-chromenes [Heterocyclic Compounds, Vol. 31, Ed. G. P. Ellis (New York 1977), page 11 et seq.] by halogenation with N-bromosuccinimide or N-chlorosuccinimide (Wohl-Ziegler reaction).

As examples of the 4-halogenomethylchromenes there may be mentioned: 4-chloromethyl-2H-chromene, 4-bromomethyl-2-methyl-2H-chromene, 4-bromomethyl-2,2-dimethylchromene, 4-bromomethyl-2-isopropyl-2H-chromene, 4-chloromethyl-2,2-diethylchromene, 4-chloromethyl-2-methyl-2-propyl-chromene, 4-bromomethyl-2-hexyl-2H-chromene, 4-bromomethyl-2-cyclopentyl-2H-chromene, 4-bromomethyl-2-cyclohexyl-2H-chromene, 4-bromomethyl-2-spirocyclopentachromene, 4-bromomethyl-2-spirocyclohexachromene, 4-bromomethyl-6-methyl-2-spirocyclopentachromene, 4-bromomethyl-7-methyl-2-spirocyclopentachromene, 4-bromomethyl-6,8-dimethyl-2-spirocyclopentachromene, 4-bromomethyl-3-chloro-2-spirocyclopentachromene, 4-bromomethyl-6-methoxy-2-spirocyclopentachromene, 4-bromomethyl-7-methoxy-2-spirocyclopentachromene, 4-bromomethyl-7-isopropoxy-2-spirocyclopentachromene, 4-bromomethyl-7-phenoxy-2-spirocyclopentachromene, 4-bromomethyl-7-benzyloxy-2-spirocyclopentachromene, 4-bromomethyl-7-phenyl-2-spirocyclopentachromene, 4-bromomethyl-6-methyl-2,2-dimethylchromene, 4-bromomethyl-6-chloro-2,2-dimethylchromene, 4-bromomethyl-7-methoxy-2,2-dimethylchromene, 4-bromomethyl-6-methyl-2-spirocyclohexachromene and 4-bromomethyl-7-methoxy-2-spirocyclohexachromene.

The chroman and chromene derivatives according to the invention surprisingly show an anti-hypertensive action and can therefore be employed, in the free form or in the form of their pharmaceutically acceptable acid addition salts, as medicaments.

The novel compounds have a broad and diverse pharmacological action spectrum and a surprisingly long duration of action.

Specifically, the following principal actions were demonstrable in animal experiments:

1. The tone of the smooth muscle of the vessels is greatly lowered under the action of the compounds. This vascular-spasmolytic action may occur in the entire vascular system or manifest itself in a more or less isolated manner in circumscribed vascular regions (such as, for example, the central nervous system). The compounds are therefore particularly suitable for use as cerebral therapeutic agents.

2. The compounds lower the blood pressure of hypertonic animals and can accordingly be used as anti-hypertensive agents.

By virtue of these properties the compounds according to the invention are suitable for the treatment of ischaemic cardiac disorders in the broadest sense, for the therapy of hypertension and for the treatment of cerebral and peripheral blood circulation disturbances.

The new active compounds can be converted in a known manner into the customary formulations, such as tablets, capsules, dragees, pills, granules, aerosols, syrups, emulsions, suspensions and solutions, using inert, non-toxic pharmaceutically suitable excipients or solvents. The therapeutically active compound should in each case be present in a concentration of about 0.5 to 90% by weight of the total mixture, that is to say in amounts which suffice to achieve the dosage range indicated.

The formulations are prepared, for example, by extending the active compounds with solvents and/or excipients, optionally with the use of emulsifiers and/or dispersing agents and, for example when using water as a diluent, organic solvents can optionally be used as auxiliary solvents.

Examples of auxiliary substances which may be mentioned are: water, non-toxic organic solvents, such as paraffins (for example petroleum fractions), vegetable oils (for example groundnut oil/sesame oil), alcohols (for example ethyl alcohol and glycerol), glycols (for example propylene glycol and polyethylene glycol), solid excipients, such as, for example, natural rock powders (for example kaolins, aluminas, talc and chalk), synthetic rock powders (for example highly disperse silica and silicates), sugars (for example cane sugar, lactose and glucose), emulsifiers (for example polyoxyethylene fatty acid esters, polyoxyethylene fatty alcohol ethers, alkylsulphonates and arylsulphonates), dispersing agents (for example lignin, sulphite waste liquors, methylcellulose, starch and polyvinylpyrrolidone) and lubricants (for example magnesium stearate, talc, stearic acid and sodium lauryl-sulphate).

Administration is effected in the customary manner, preferably orally or parenterally, especially perlingually or intravenously. In the case of oral use the tablets can, of course, also contain, in addition to the excipients mentioned, additives such as sodium citrate, calcium carbonate and dicalcium phosphate, together with various additional substances such as starch, preferably potato starch, gelatin and the like. Furthermore, lubricants, such as magnesium stearate, sodium laurylsulphate and talc can be co-used when making tablets. In the case of aqueous suspensions and/or elixirs which are intended for oral use, the active compounds can be mixed with various flavour-improving agents or colourants in addition to the abovementioned auxiliary substances.

In the case of parenteral use, solutions of the active compounds, employing suitable liquid excipients, can be used.

In general it has proved advantageous, in the case of intravenous administration, to administer amounts of about 0.001 to 10 mg/kg, preferably about 0.05 to 5 mg/kg of body weight daily to achieve effective results, and in the case of oral administration the dosage is about 0.5 to 30 mg/kg, preferably 1 to 10 mg/kg of body weight daily.

Nevertheless it can at times be necessary to deviate from the amounts mentioned, and in particular to do so as a function of the body weight of the experimental animal or of the nature of the administration method, but also because of the species of animal and the individual behaviour towards the medicament, and the nature of the formulation of the medicament and the time at which, or interval over which, the administration takes place. Thus it can suffice, in some cases, to manage with less than the abovementioned minimum amount, whilst in other cases the upper limit mentioned must be exceeded. Where relatively large amounts are administered, it can be advisable to divide these into several individual administrations over the course of the day. The same dosage range is envisaged for administration in human medicine. The general sense of the above comments also applies again.

EXAMPLES OF THE PREPARATION OF INTERMEDIATES FOR PREPARATION VARIANT B

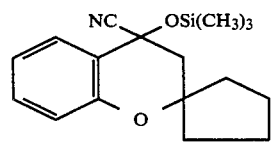

1.

30 ml of boron trifluoride etherate are added dropwise to a mixture of 528 g (4.8 mol) of trimethylsilyl cyanide and 969 g (4.8 mol) of 2-spirocyclopentachroman-4-one with cooling and stirring, at a rate such that the temperature does not exceed 40°–50°; the mixture is then stirred for 5 hours at room temperature and left to stand overnight. Thereafter it is degassed in a high vacuum at a temperature of 50°. By this means, the product is obtained as a viscous oil, in 85–95% yield according to gas chromatography. It is sufficiently pure for further reactions.

The following were prepared in a similar manner:

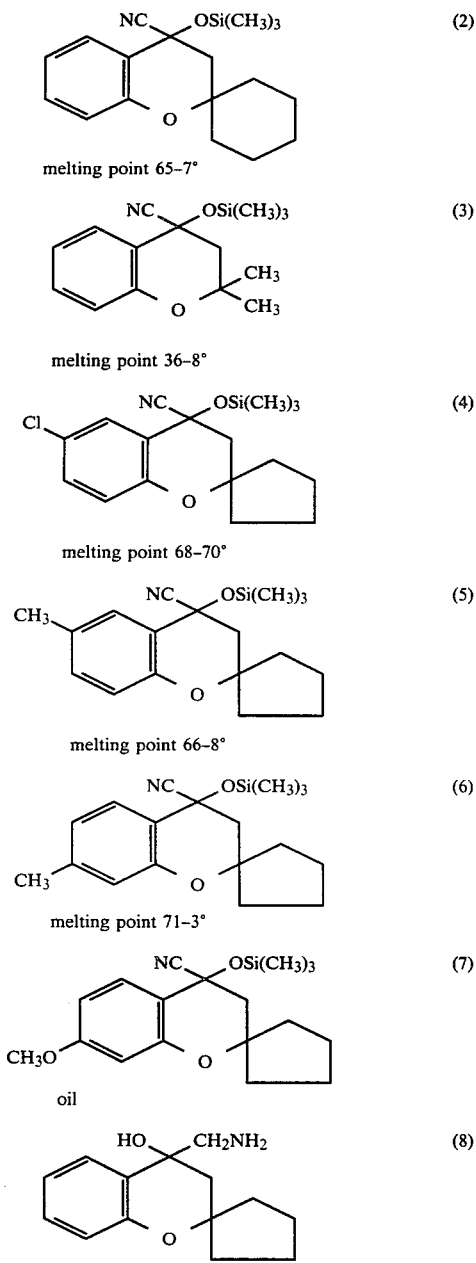

16.4 g of lithium aluminium hydride are mixed with 600 ml of dry tetrahydrofuran and a solution of 120 g of 2-spirocyclopenta-4-cyano-4-trimethylsilyloxy-chroman (89% pure) in 120 ml of dry tetrahydrofuran is added dropwise, whilst stirring and cooling with acetone/solid carbon dioxide. (Nitrogen atmosphere, exclusion of moisture, internal temperature <20° C.).

The mixture is allowed to come to room temperature whilst being stirred, is then heated for 3 hours to the reflux temperature, and is allowed to cool. 16.4 g of water are cautiously added dropwise, followed by 49.2 g of 15% strength potassium hydroxide solution. After the mixture has stood overnight it is filtered, the mother liquor is concentrated in vacuo and the residue is triturated with 135 ml of ether. The white crystalline product obtained is filtered off. 35–57 g are obtained. The ethereal mother liquor is concentrated and the residue taken up in 100 ml of methanol, boiled with a small amount of potassium hydroxide for 1 hour and worked up. This method serves to complete the silyl ether hydrolysis. In this way, a total of 66 g of white crystals (82% of theory) are obtained; melting point 119° C.

The following were prepared in a similar manner:

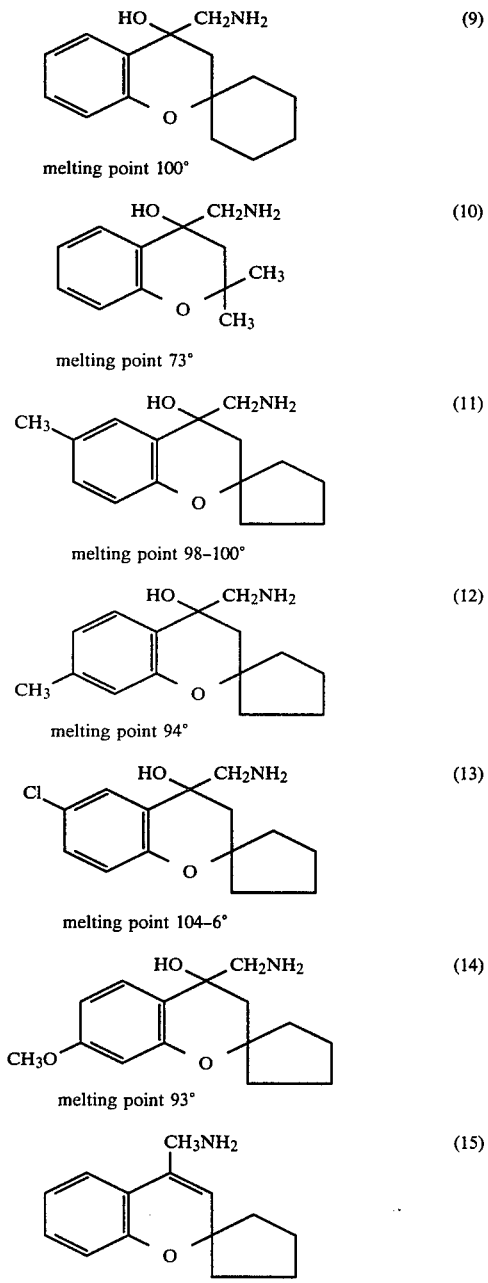

2 liters of toluene and 190 g of toluenesulphonic acid monohydrate are boiled under a water separator until azeotropic drying is complete. 233 g (1 mol) of 2-spirocyclopenta-4-hydroxy-4-aminomethylchroman are added to the cooled mixture and the whole is heated to the boil for 5 hours, during which about 18 cc of water are separated off. After the mixture has cooled, a small amount of solid is filtered off and the toluene phase is stirred with excess concentrated sodium hydroxide solution. After phase separation, the toluene solution is washed with water and worked up in the usual manner. 140 g (65% of theory), boiling point 147–70/0.7–1.2 mm Hg.

The following were prepared in a similar manner:

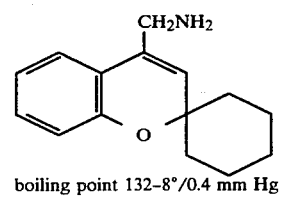

boiling point 132–8°/0.4 mm Hg (16)

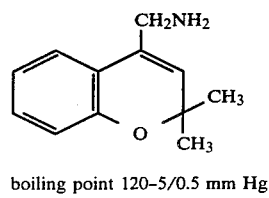

boiling point 120–5/0.5 mm Hg (17)

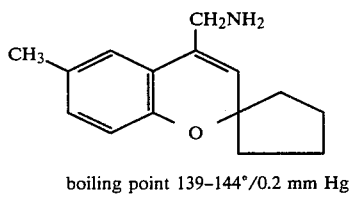

boiling point 139–144°/0.2 mm Hg (18)

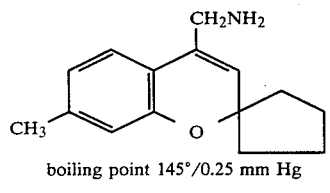

boiling point 145°/0.25 mm Hg (19)

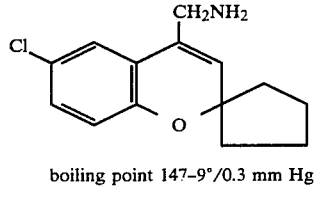

boiling point 147–9°/0.3 mm Hg (20)

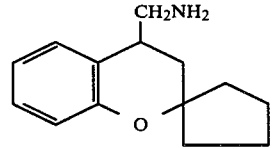

(21)

50 g of 2-spirocyclopenta-4-aminomethyl-chrom-3-ene, in the presence of 300 ml of methanol and 10 g of Raney nickel, are catalytically hydrogenated for about 4.5 hours in a pressure autoclave at 60° and 100 bar H$_2$ pressure. The catalyst is then filtered off and the filtrate is concentrated and fractionated.

Boiling point 150°–54°/0.9 mm Hg; 40 g of colourless liquid (about 80% of theory).

The following were prepared in a similar manner:

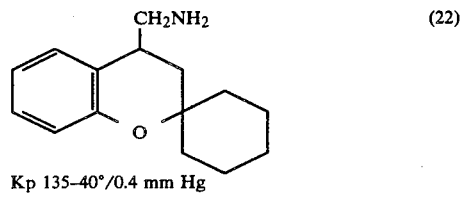

Kp 135–40°/0.4 mm Hg (22)

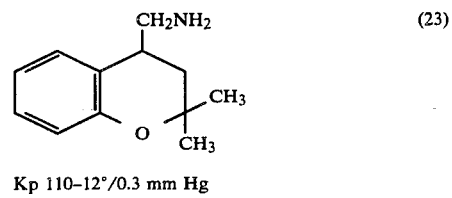

Kp 110–12°/0.3 mm Hg (23)

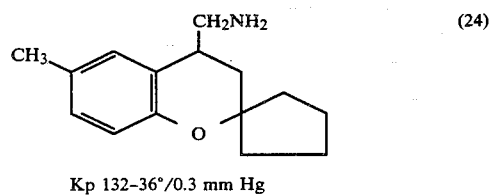

Kp 132–36°/0.3 mm Hg (24)

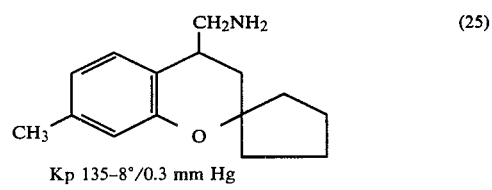

Kp 135–8°/0.3 mm Hg (25)

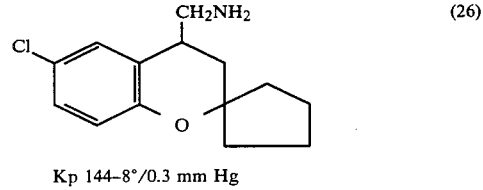

Kp 144–8°/0.3 mm Hg (26)

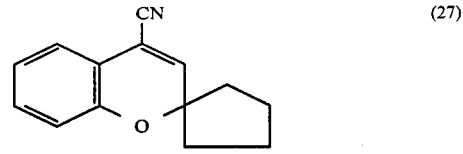

(27)

429 g of 2-spirocyclopenta-4-cyano-4-trimethylsilyloxy-chroman (89% strength) are introduced into 2.2 liters of absolute pyridine. 694 g of phosphorus oxychloride are added dropwise, resulting in a slightly exothermic reaction. The mixture is heated to the boil *slowly*, since the reaction becomes more vigorous on warming. After having been boiled under reflux for 10 hours and cooled, the batch is cautiously poured onto a mixture of about 6 liters of crushed ice and 1 liter of concentrated hydrochloric acid. The precipitate formed is filtered off, washed with water and taken up in toluene; the toluene solution is shaken with active charcoal and extracted by shaking with sodium bicarbonate solution. After the solution has been dried with sodium sulphate, the toluene is evaporated off in vacuo and the residue is crystallised from methylcyclohexane, in the presence of active charcoal; 180 g (67% of theory) are obtained as pale grey crystals of melting point 50°. The product can be distilled. Boiling point 135°/0.2 mm Hg. Melting point of the pure white crystals: 58°–59°.

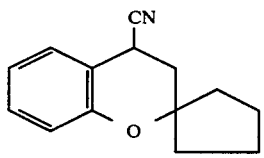
(28)

400 g of 2-spirocyclopenta-4-cyano-chromen-3-ene in 1,800 ml of tetrahydrofuran are hydrogenated over 40 g of palladium on charcoal (5% strength) at 40°–45° under 50 bar pressure. After conventional working-up, 360 g (~90% of theory) of white crystals, of boiling point 131°–5°/0.3 mm and melting point 44°–5°, are obtained.

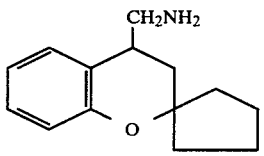
(29)

50 g of 2-spirocyclopenta-4-cyanochroman, in the presence of 200 ml of methanol, 50 ml of liquid ammonia and 10 g of Raney cobalt are catalytically hydrogenated for about 3.5 hours in a pressure autoclave at 90° C. and 100 bar $H_2$ pressure. The catalyst is then filtered off and the filtrate is concentrated and fractionated.

Boiling point 130°–140°/0.35 mm Hg; 40 g of colourless liquid (about 80% of theory) (identical with the product from Example 21).

EXAMPLES OF THE PREPARATION OF INTERMEDIATES OF PREPARATION VARIANT C

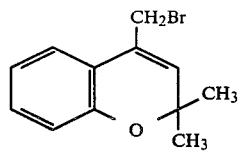
(30)

176 g (1 mol) of 2,2,4-trimethylchromene are dissolved in 1 liter of carbon tetrachloride which has been dried over phosphorus pentoxide and 178 g (1 mol) of N-bromo-succinimide and 2 g of azo-bis-isobutyronitrile are added. The mixture is slowly heated to the boil and is boiled for 1 hour. When it has cooled, the precipitate is filtered off (succinimide). The mother liquor is concentrated in vacuo. 255 g of a brown oil which is 89% pure according to gas chromatography (~90% of theory) are obtained; the material can be employed directly for further reactions. The product distills at 105°–9°/0.28 mm. It can be characterised as the pyridinium bromide (melting point 186°–7°).

The following was prepared in a similar manner:

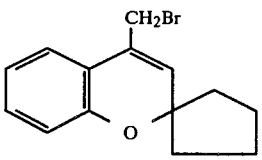
(31)

Oil, not stable to distillation; melting point of the pyridinium bromide 165°–7°.

EXAMPLES ACCORDING TO THE INVENTION

(32) Preparation according to process variant A

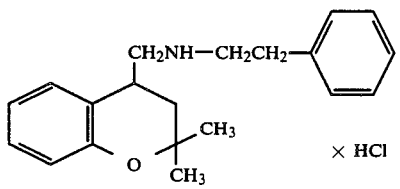

12.1 g (0.1 mol) of phenylethylamine are added to 19.0 g (0.1 mol) of 2,2-dimethyl-4-formyl-chroman in 100 ml of methanol, whilst stirring at room temperature, with gentle cooling, and the mixture is then stirred for 1.5 hours. Thereafter, 4.5 g of sodium boranate are added and the mixture is stirred for a further day, concentrated and worked up with ethyl acetate/water. The ethyl acetate phase is washed with water, dried and concentrated. The residue is dissolved in ether and dry hydrogen chloride is passed through the solution. The precipitate formed is filtered off, stirred with water and filtered off. It is dried and recrystallised from acetonitrile. 20.5 g of white crystals (62% of theory), of melting point 180°–3°.

(33) Preparation according to process variant B

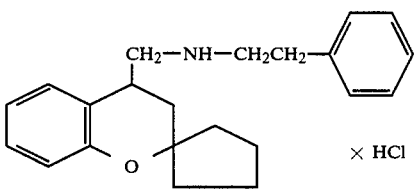

12 g (0.1 mol) of phenylacetaldehyde are reacted with 21.7 g (0.1 mol) of 2-spirocyclopenta-4-aminomethylchroman and worked up, as in the example given above. 19.5 g (55% of theory) of white crystals, of melting point 202°–3°.

(34) Preparation according to process variant B

A solution of 6.5 g of 2,2-spirocyclopenta-4-aminomethylchrom-3-ene and 6.5 g of 4-m-trifluoromethylphenyl-butan-2-one in 30 ml of toluene is heated to the boil under a water separator for 30 minutes and then concentrated to 50°/10 mm Hg. The oily residue is dissolved in 50 ml of tetrahydrofuran and added dropwise, at about 20° C., to a suspension of 5 g of LiAlH₄ in 150 ml of THF. The mixture is then stirred for 5 hours at the reflux temperature and is cooled to 10° C.; 5 ml of water and 15 ml of 15% strength potassium hydroxide solution are successively added cautiously, and this mixture is stirred for 1 hour at 20° and then filtered. The filtrate is concentrated and the concentrate distilled. Yield: 6.6 g of almost colourless oil, boiling point 200°-210°/0.03 mm Hg.

(35) Preparation according to process variant C

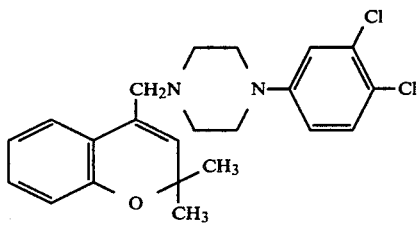

25 g (0.11 mol) of N-3,4-dichlorophenyl-piperazine and 11.1 g (0.11 mol) of triethylamine are together introduced into 55 ml of toluene, and 27.8 g (0.11 mol) of 2,2-dimethyl-4-bromomethylchrom-3-ene are added dropwise. In the course thereof, a precipitate separates out and the temperature rises to about 45° C. Stirring is continued for 3 hours and the mixture is left to stand overnight. It is then thoroughly stirred with excess 2N sodium hydroxide solution and the toluene phase is separated off, washed with water and dried with sodium sulphate. After the solvent has been distilled off, the product starts to precipitate. The crystallisation is completed by adding petroleum ether. After filtering off the product and drying it, 27.5 g (62% of theory) of white crystals, of melting point 108° C., are obtained.

The following were prepared in a similar manner:

(36) according to processes A and B

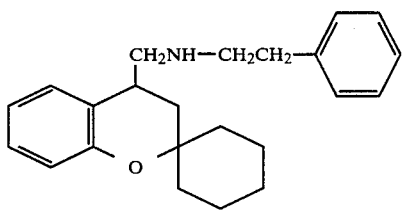

Boiling point 175°-8°/0.2 mm Hg.

(37) according to processes A and B

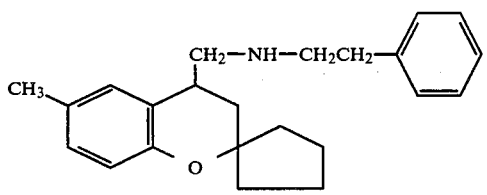

Melting point of the hydrochloride 253°-6°.

(38) according to processes A and B

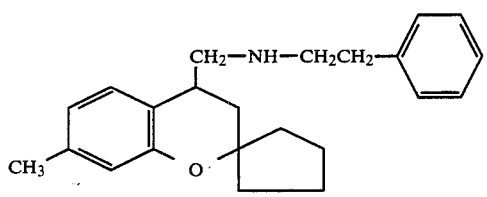

Melting point of the hydrochloride 245°-8°.

(39) according to processes A and B

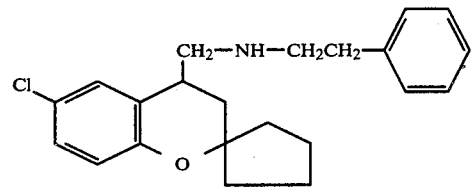

Boiling point 180°-5°/0.15 mm Hg.

(40) according to processes A and B

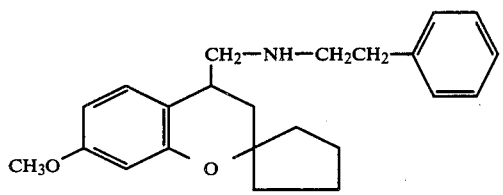

Melting point of the hydrochloride 220°-3°.

(41) according to processes A and B

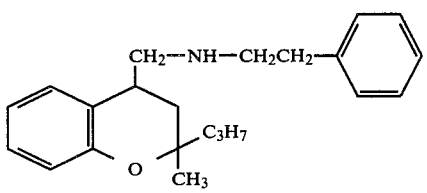

Boiling point 175°-9°/0.25 mm Hg.

(42) according to processes A and B

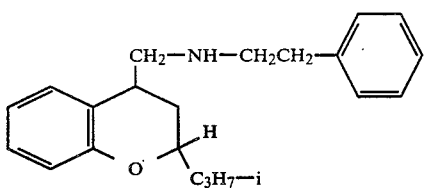

Boiling point 172°-7°/0.25 mm Hg.

(43) according to processes A and B

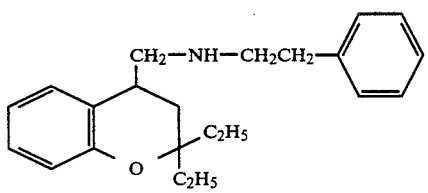

Boiling point 190°-5°/0.65 mm Hg.

(44) according to processes A and B

Resin.
(45) according to processes A and B

Melting point of the hydrochloride 180°-2°.
(46) according to processes A and B

Melting point of the hydrochloride 198°-200°.
(47) according to processes A and B Melting point of the hydrochloride 214°-6°.
(48) according to processes A and B Melting point of the hydrochloride 212°.
(49) according to processes A and B Melting point of the hydrochloride 190°.
(50) according to processes A and B Melting point of the hydrochloride 231°.
(51) acccording to processes A and B Boiling point 198°-203°/0.1 mm Hg.
(52) according to processes A and B Boiling point 183°-190°/0.15 mm Hg.
(53) according to processes A and B Boiling point 171°-7°/0.15 mm Hg.
(54) according to processes A and B

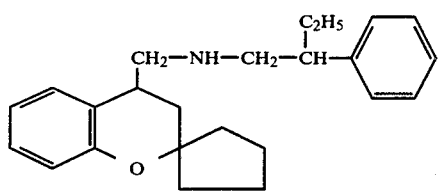

Boiling point 184°-9°/0.4 mm Hg.
(55) according to processes A and B

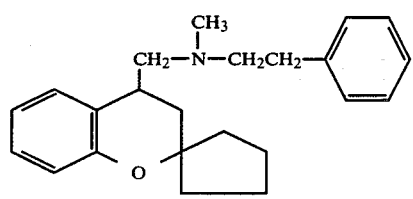

Boiling point 168°-75°/0.25 mm Hg.
(56) according to processes A and B

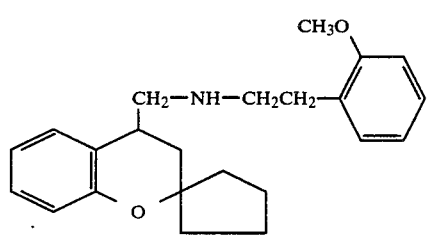

Melting point of the hydrochloride 208°-10°.
(57) according to processes A and B

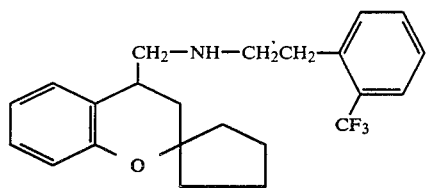

Boiling point 185°-95°/0.1 mm Hg.
(58) according to processes A and B

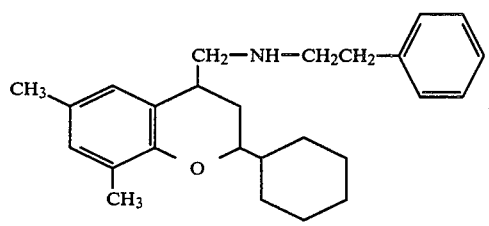

Boiling point 188°-94°/0.15 mm Hg.
(59) according to processes A and B

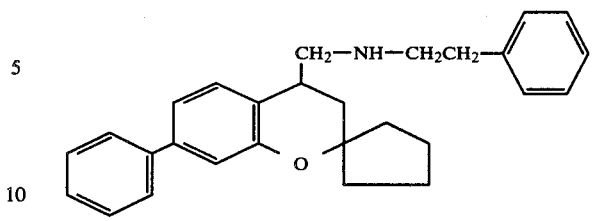

Resin.
(60) according to process A

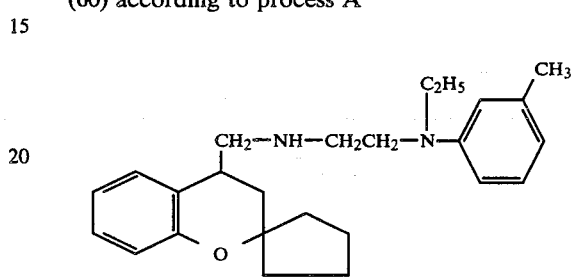

Boiling point 190°-6°/0.2 mm Hg.
(61) according to process A

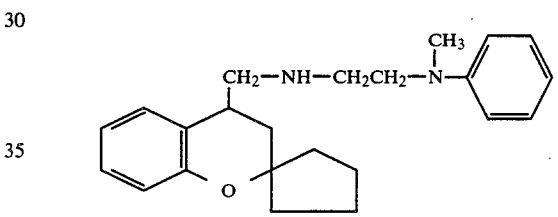

Boiling point 181°-3°/0.15 mm Hg.
(62) according to process A

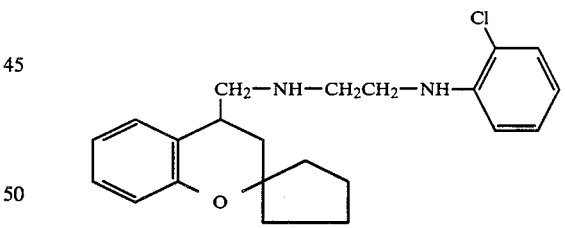

Boiling point 195°-202°/0.25 mm Hg.
(63) according to process A

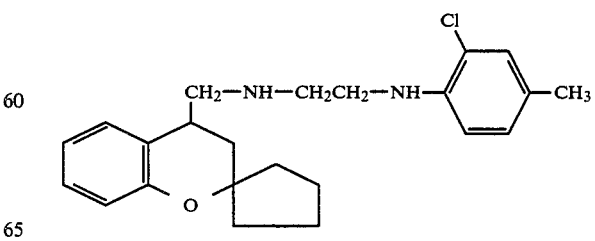

Melting point of the hydrochloride 170°-2°.
(64) according to process A

Melting point of the hydrochloride 168°–70°.
(65) according to process A

Melting point of the hydrochloride 185°.
(66) according to process A

Melting point of the hydrochloride 202°–4°.
(67) according to processes A and B

Boiling point 178°–82°/0.15 mm Hg.
(68) according to processes A and B

Boiling point 185°–7°/0.2 mm Hg.
(69) according to processes A and B

Melting point of the hydrochloride 185°–7°.
(70) according to processes A and B

Melting point of the hydrochloride 102°–4°.
(71) according to processes A and B

Boiling point 198°–205°/0.15 mm Hg.
(72) according to processes A and B

Boiling point 207°–15°/0.15 mm Hg.
(73) according to process C

Melting point 93°–4°.
(74) according to process C

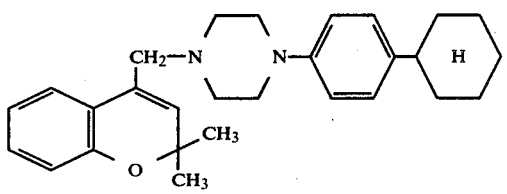

Melting point 120°–1°.
(75) according to process C

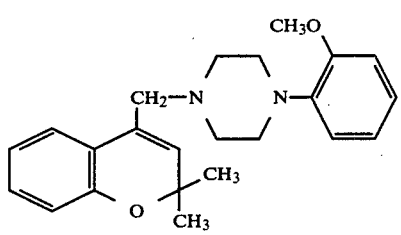

Melting point 94°–6°.
(76) according to process C

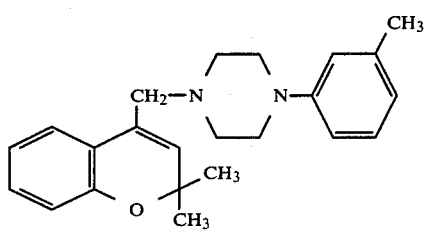

Melting point 92°–3°.
(77) according to process C

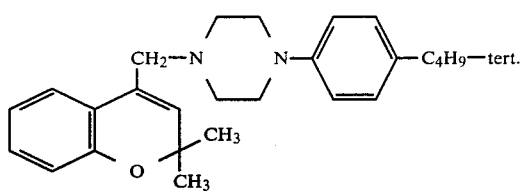

Melting point 67°–9°.
(78) according to process C

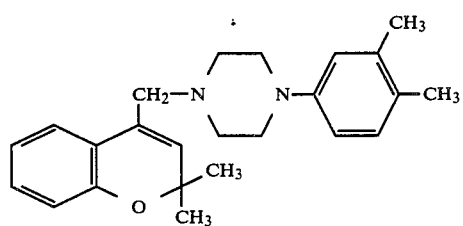

Melting point 88°–9°.
(79) according to process C

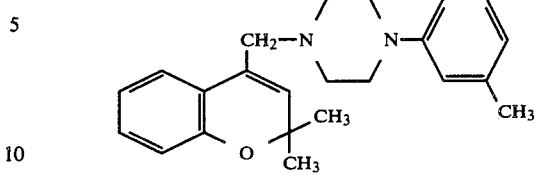

Boiling point 193°–9°/0.3 mm Hg.
(80) according to process C

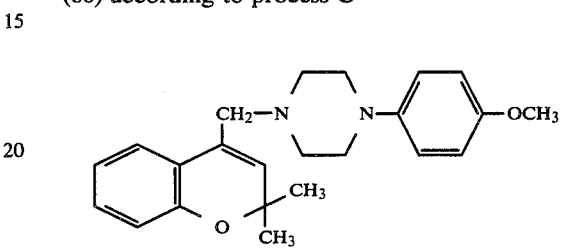

Melting point 88°.
(81) according to process C

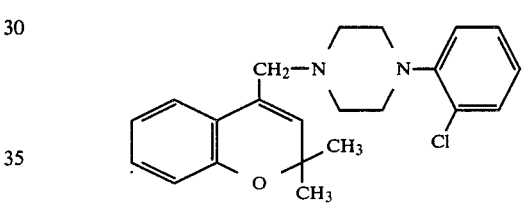

Melting point 72°.
(82) according to process C

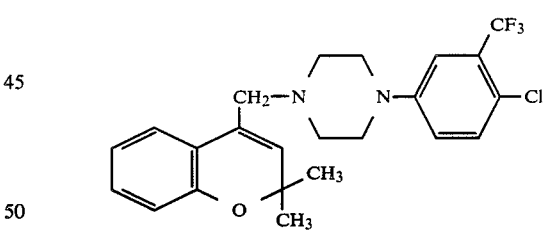

Melting point 104°–5°.
(83) according to process C

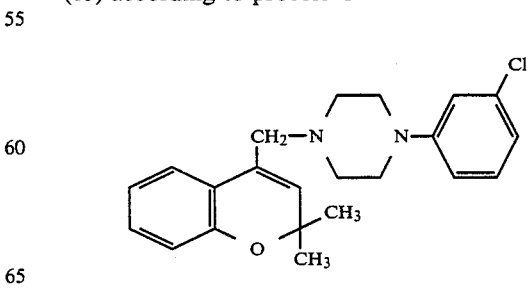

Melting point 77°.
(84) according to process C

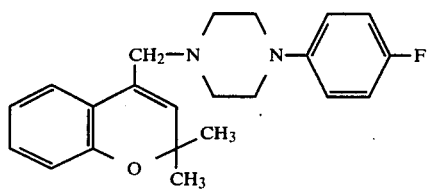

Melting point 146°.
(85) according to process C

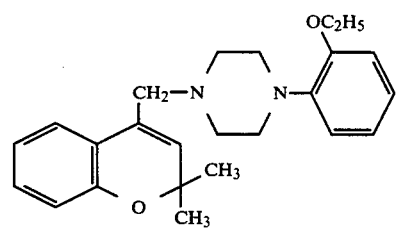

Melting point 83°.
(86) according to process C

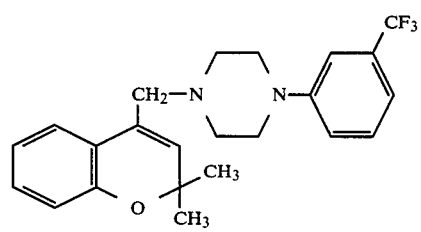

Boiling point 192°-8°/0.15 mm Hg.
(87) according to process C

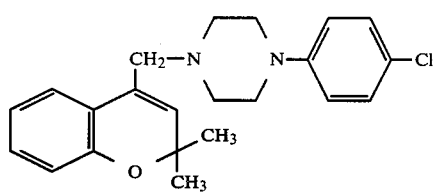

Melting point 121°.
(88) according to process C

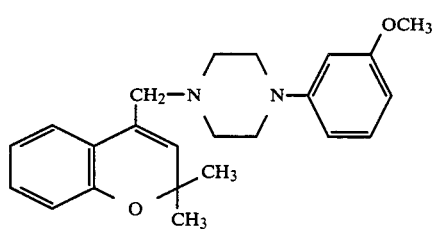

Melting point 84°.
(89) according to process C

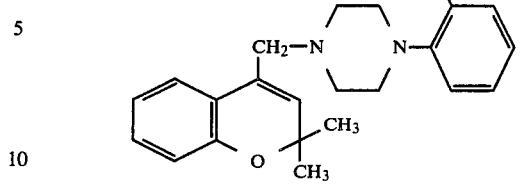

Boiling point 189°-94°/0.1 m Hg.
(90) according to process C

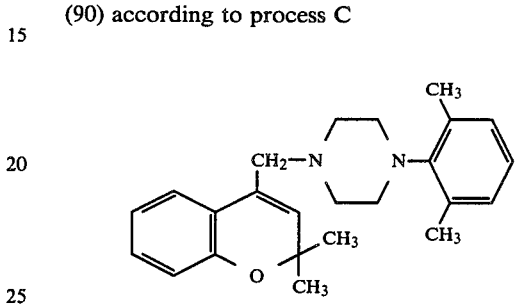

Boiling point 191°-9°/0.2 mm Hg.
(91) according to process C

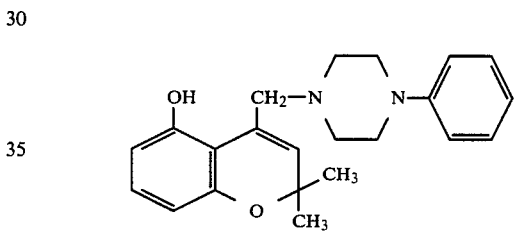

Melting point 170°-1°.
(92) according to process A

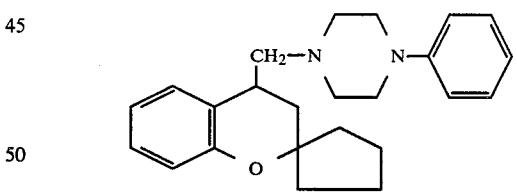

Boiling point 180°-4°/0.15 mm Hg.
(93) according to process C

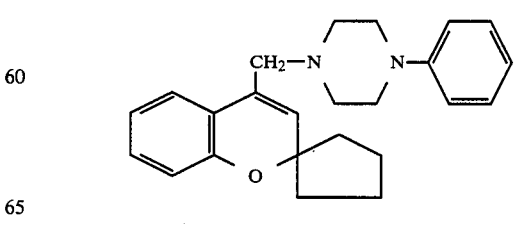

Melting point 117°-9°.
(94) according to process C

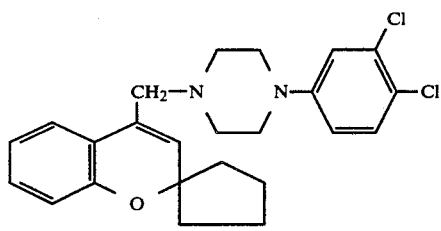

Melting point 118°–20°.
(95) according to process C

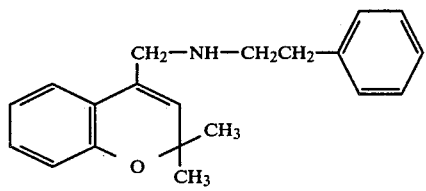

Boiling point 198°–203°/0.8 mm Hg.
(96) according to processes B and C

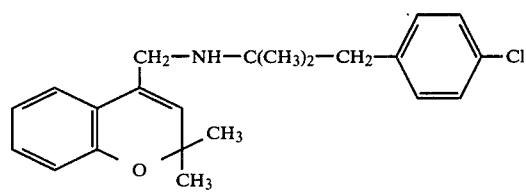

Boiling point 175°–80°/0.2 mm Hg.
(97) according to processes A and B

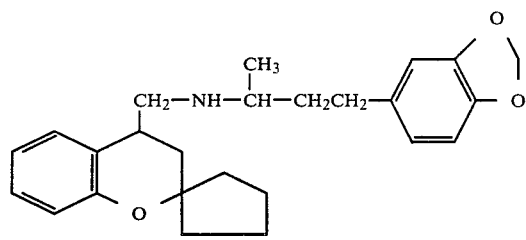

Boiling point 191°–6°/0.1 mm Hg.
(98) according to processes A and B

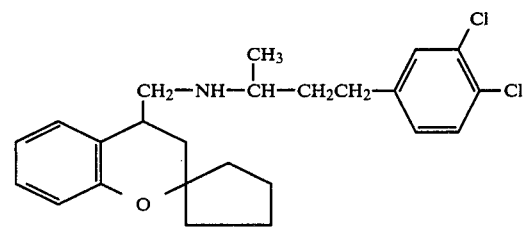

Boiling point 201°–212°/0.2 mm Hg.
(99) according to processes A and B

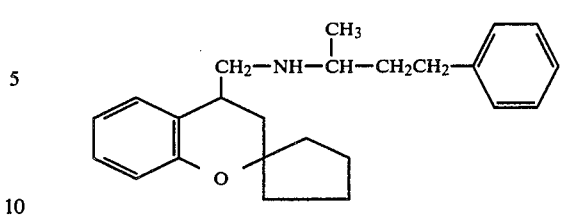

Boiling point 182°–7°/0.2 mm Hg.
(100) according to processes A and B

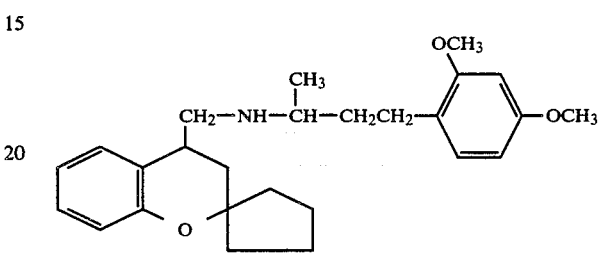

Boiling point 205°–9°/0.1 mm Hg.
(101) according to processes A and B

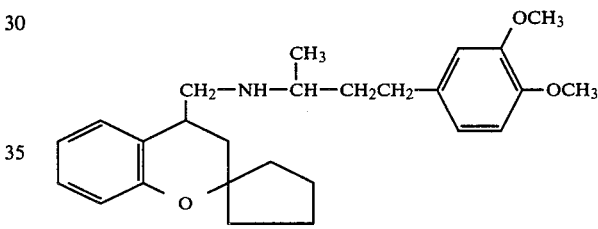

Boiling point 202°–10°/0.15 mm Hg.
(102) according to processes A and B

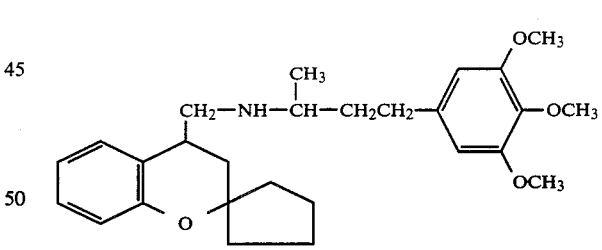

Boiling point 204°–12°/0.1 mm Hg.
(103) according to processes A and B

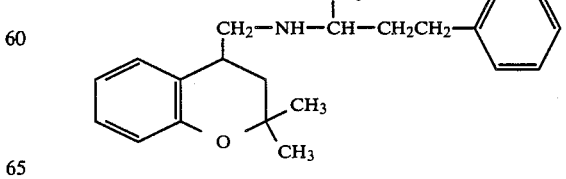

Boiling point 171°–4°/0.1 mm Hg.
(104) according to processes A and B

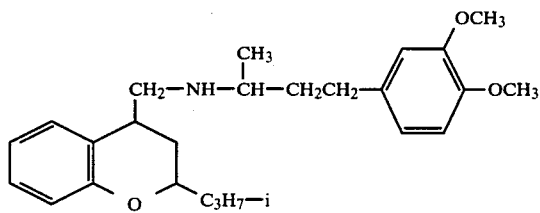

Boiling point 189°–96°/0.1 mm Hg.
(105) according to processes A and B

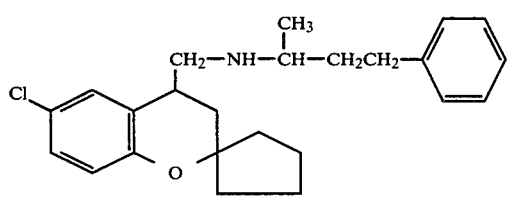

Boiling point 190°–8°/0.2 mm Hg.
(106) according to processes A and B

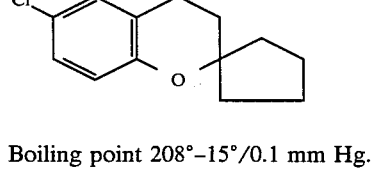

Boiling point 208°–15°/0.1 mm Hg.
(107) according to processes A and B

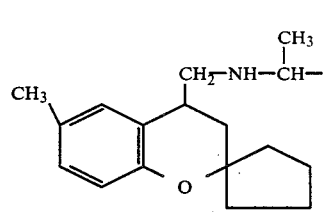

Boiling point 198°–206°/0.1 mm Hg.
(108) according to processes A and B

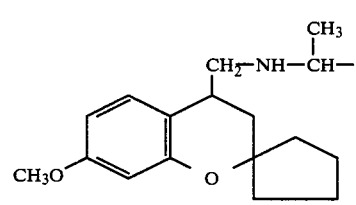

Boiling point 205°–12°/0.1 mm Hg.
(109) according to processes A and B

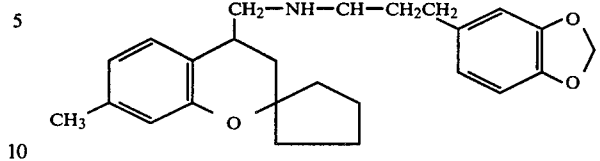

Boiling point 200°–5°/0.15 mm Hg.
(110) according to processes A and B

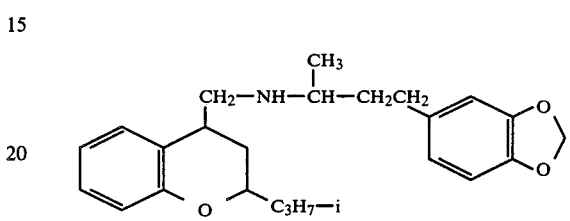

Boiling point 185°–92°/0.1 mm Hg.
(111) according to processes A and B

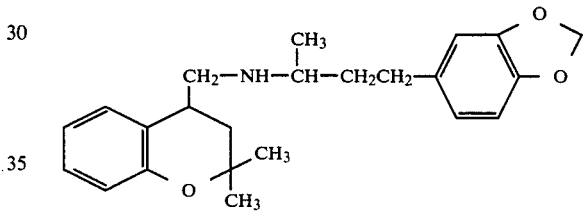

Boiling point 181°–7°/0.1 mm Hg.
(112) according to processes A and B

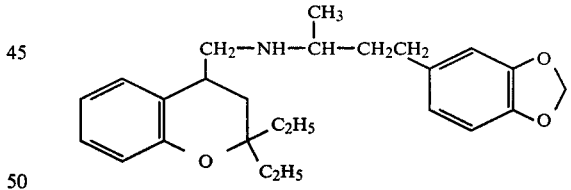

Boiling point 198°–204°/0.15 mm Hg.
(113) according to processes A and B

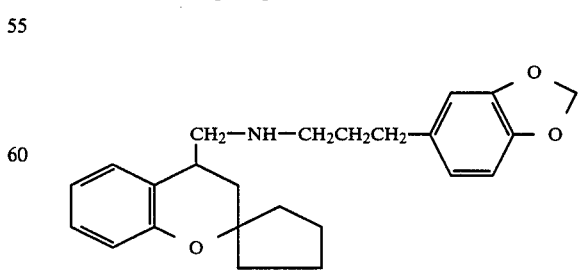

Boiling point 190°–2°/0.15 mm Hg.
(114) according to processes A and B

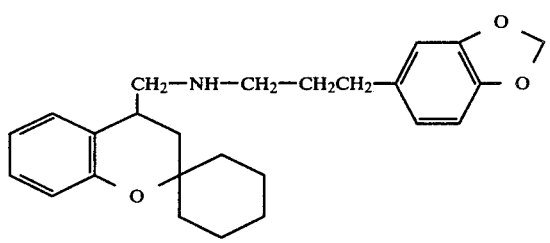

Boiling point 199°–204°/0.1 mm Hg.
(115) according to processes B and C

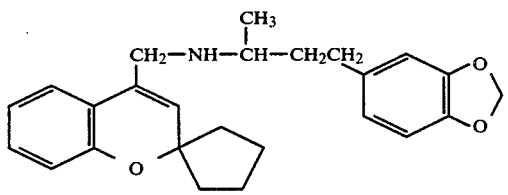

Boiling point 210°–215°/0.1 mm Hg.
(116) according to processes A and B

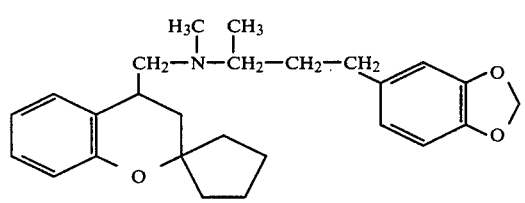

Boiling point 215°–8°/0.1 mm Hg.
(117) according to processes B and C

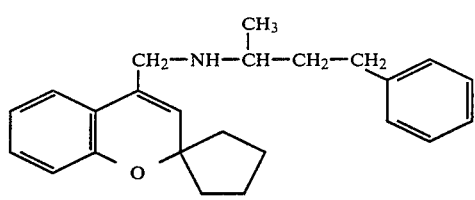

Boiling point 200°–205°/0.1 mm Hg.
(118) according to processes A and B

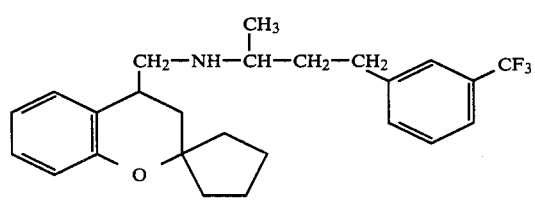

Boiling point 195°–200°/0.05 mm Hg.
(119) according to processes B and C

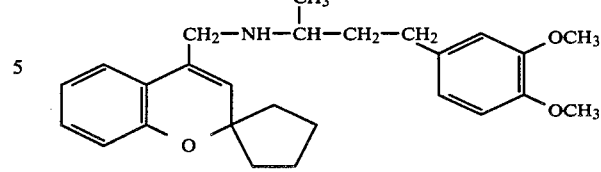

Boiling point 220°/0.12 mm Hg.
(120) according to processes A and B

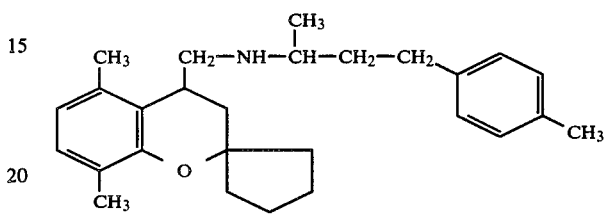

Boiling point 240°/0.1 mm Hg.

EXAMPLES OF THE PREPARATION OF CHROMAN-4-CARBALDEHYDES (STARTING PRODUCT FOR PREPARATION VARIANT A)

Example 121

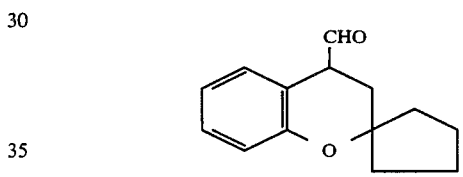

A mixture of 12 g of $Rh[(C_6H_5)_3P]Cl_3$, 96 g of triphenylphosphine and 660 ml of toluene is introduced into a 3 liter stainless steel autoclave and a mixture of 665 g (3.58 mol) of 2-spirocyclopentachrom-3-ene is pumped in slowly in the course of 6 hours at 160°–70° C. internal temperature and a $CO/H_2$ pressure of initially 150 and later 300 bar. The mixture is stirred for a further hour at 170° C. and is distilled after the pressure has been released. 327 g (42% of theory) of 2-spirocyclopentachroman-4-carbaldehyde are obtained as an almost colourless liquid of boiling point 127°–30°/0.1 mm Hg.

Example 122

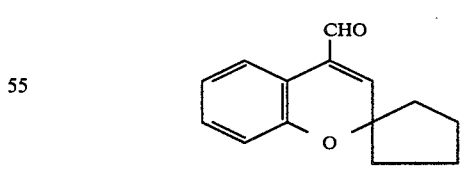

0.083 g of $Rh[(C_6H_5-CH_2)_2S]_3Cl_3$ and 500 ml of toluene are stirred for 1 hour in an autoclave at 170° and 170 bar $CO/H_2$ pressure. The mixture is allowed to cool to 135° and 558 g (3 mol) of 2-spirocyclopentachrom-3-ene, dissolved in 600 ml of toluene, are pumped in over the course of 3 hours, whilst maintaining a pressure of 250–280 bar. After the mixture has been cooled, brought to atmospheric pressure and degassed, the solvent is stripped off in vacuo and the liquid residue is fractionated. 518 g (80% of theory) of colourless liquid, of boiling point 127°-30°/0.3 mm Hg.

The following were prepared in a similar manner to that described in Example 122.

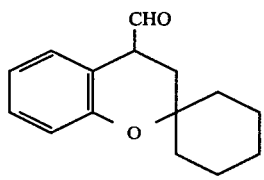
(123)

Boiling point 120°-5°/0.3 mm Hg.

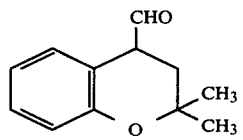
(124)

Boiling point 90°-95°/0.5 mm Hg.

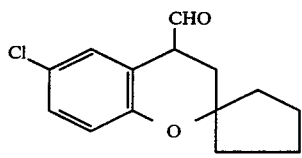
(125)

boiling point 120°/0.2 mm Hg.

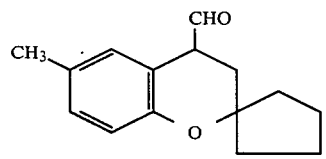
(126)

Boiling point 106°-10°/0.04 mm Hg.

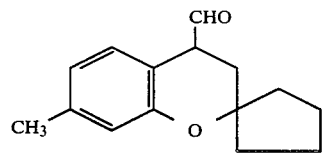
(127)

Boiling point 121°-6°/0.3 mm Hg.

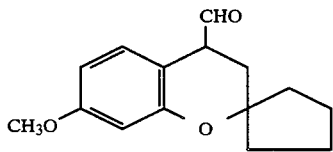
(127)

Boiling point 143°-50°/0.15 mm Hg.

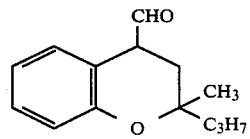
(128)

Boiling point 110°/0.05 mm Hg.

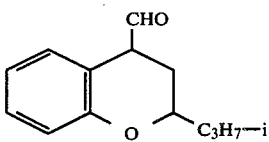
(129)

Boiling point 110°/0.5 mm Hg.

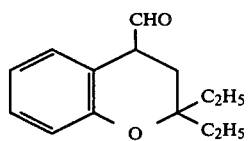
(130)

Boiling point 110°-5°/0.5 mm Hg.

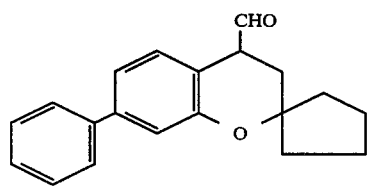
(131)

Boiling point 165°-70°/0.05 mm Hg.

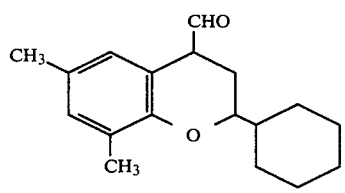
(132)

Boiling point 110°-115°/0.2 mm Hg.

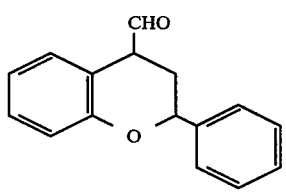
(134)

Boiling point 145°-50°/0.1 mm Hg.

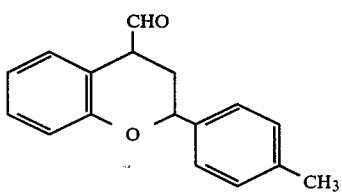
(135)

Boiling point 152°-157°/0.1 mm Hg.

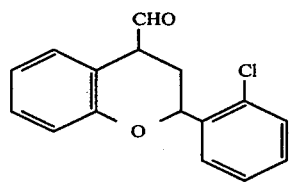 (136)
Boiling point 161°–3°/0.05 mm Hg.
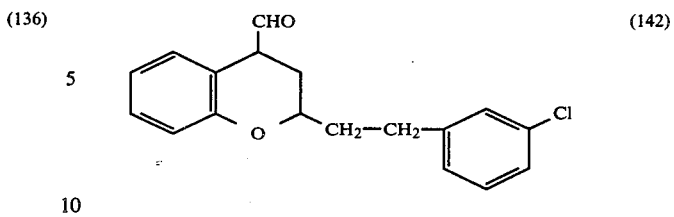 (142)
Boiling point 170°–8°/0.08 mm Hg.
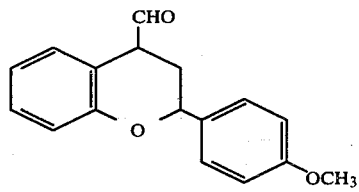 (137)
Boiling point 155°–162°/0.09 mm Hg.
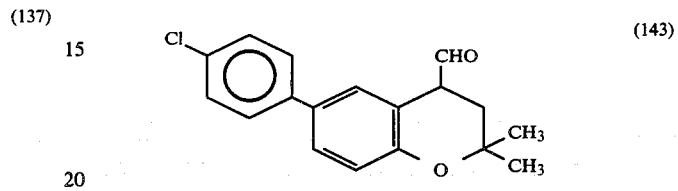 (143)
Boiling point 173°–5°/0.05 mm Hg.
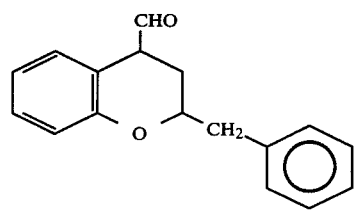 (138)
Boiling point 154°–61°/0.1 mm Hg.
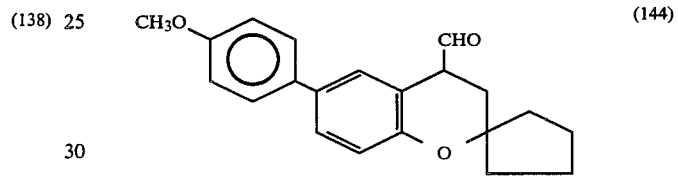 (144)
Boiling point 182°–9°/0.05 mm Hg.
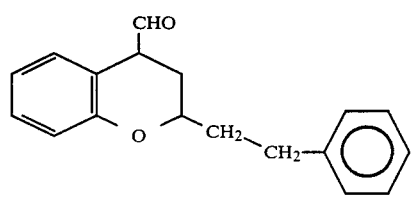 (139)
Boiling point 152°–9°/0.3 mm Hg.
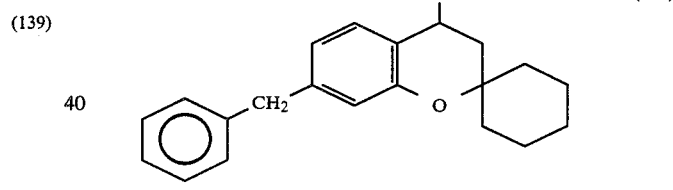 (145)
Boiling point 180°–6°/0.04 mm Hg.
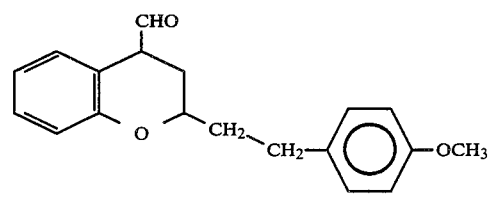 (140)
Boiling point 159°–66°/0.07 mm Hg.
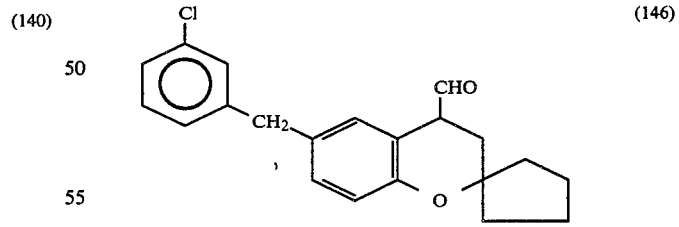 (146)
Boiling point 189°–93°/0.04 mm Hg.
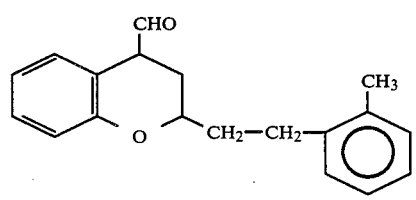 (141)
Boiling point 163°–9°/0.05 mm Hg.
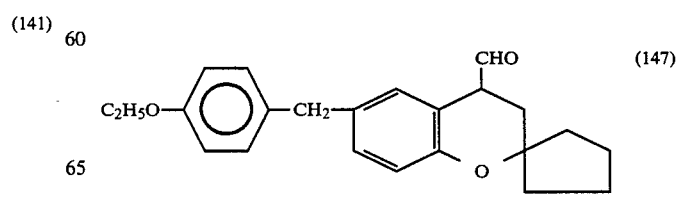 (147)
Boiling point 188°–98°/0.05 mm Hg.

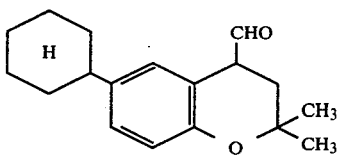
(148)

Boiling point 160°–6°/0.06 mm Hg.

Example 122 was repeated, using the following catalysts:
(a) CO₂(CO)₈
(b) [Rh(CO)₂Cl]₂
(c) Rh(PPH₃)₃Cl
(d) Rh(PPH₃)₃Cl
(e) Rh[[(C₂H₅)₂Fe]PPH₂]₃ Fl
(f) RhCl₃×3H₂O
(g) Rh(C₈H₁₄)₂Cl
(h) Rh(CO)₂acac₃
(i) HCo(CO)₃[P(Bu)₃]₃
(k) Rh₄(CO)₁₂
(L) Rn₃(CO)₁₂
(m) IR(CO)[PPH₃]₂Cl In all cases, a colourless liquid of boiling point 127°–30°/0.3 mm Hg was obtained in good yields.

Test of Antihypertensive Action on Renally Hypertonic Dogs

Method

Beagle hounds of both sexes are used. For a direct measurement of the blood pressure the animals are fitted with a permanent catheter in the aorta. To obtain experimental hypertension the right aorta renalis was stenosed.

The systolic and diastolic blood pressure and the heart rate are continuously recorded in conscious, freely moving hounds using a radio telemetry system. The data are received by an on-line data acquisition system (DAS 10/4; manufacturer; i.f.d. via a transceiver combination and evaluated by a programmable computer (Multi 4; manufacturer: Intertechnique). The data are delivered as hourly mean values of all the recorded blood pressure responses.

The test substances are dissolved in polyethylene glycol 400 and are administered orally in a gelatine capsule. The blood pressure is measured during a period of an hour preceding administration and for up to 16 hours following administration.

The minimum dose is the lowest dose with which a reduction in blood pressure of at least 15 mmHg is reached.

| | Results | |
|---|---|---|
| Substance | Minimum dose (mg/kg p.o.) | % reduction in blood pressure |
| Example 97 | 3,15 | 10 |
| Example 102 | 1,00 | 9 |
| Example 118 | 10,00 | 16 |

Test of the Antihypertensive Action on Spontaneously Hypertonic Rats

Method

The blood pressure is measured indirectly on the tails of conscious rats by means of an inflatable cuft and an infrasonic pulse recorder D along the BOUCKE-BRECHT method. During the whole test, including a two-hour pre-administration period, the animals are individually contained in plastic tubes heated to about 30° C. and surrounded by a water-jacket. The inflatable rubber cuft is positioned at the start of the tail and the pulse recorder at a distance of 3 cm therefrom. In order to obtain uniform measuring results for the repeated measurements the place of measurement on the tail is marked with Indian ink.

Measurements are taken when the cuft pressure falls, the pressure present in the cuft on recurrency of the pulsations being equal to the systolic blood pressure in the rats' tails.

The substances are applied orally in the form of a suspension by means of a probang. The systolic blood pressure is measured prior to administration and 1, 2, 4, 6 and 24 hours following administration of the substances. Each does is tested in at least 3 animals. On each test day an untreated group is tested parallel to the treated animals as a control means.

The minimum dose is the lowest dose at which a reduction in blood pressure of at least 15 mmHg is achieved.

| Substance | minimum dose (mg/kg p.o.) |
|---|---|
| Example 97 | 10,0 |
| Example 102 | 1,0 |

We claim:

1. A compound of the formula (I)

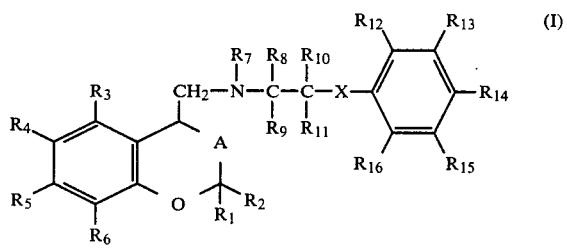

in which
—A— represents a single bond or a double bond, and
R₁ and R₂ are identical or different and represent hydrogen, C₁–C₆-alkyl, C₅–C₇-cycloalkyl, phenyl which is optionally substituted by C₁–C₄-alkyl, halogen and/or C₁–C₄-alkoxy, or C₇–C₉-aralkyl, whose aryl radical is optionally substituted by C₁–C₄-alkyl, halogen and/or C₁–C₄-alkoxy, or R₁ and R₂ conjointly with the enclosed C atom of the chroman ring form a 4-membered to 7-membered carbocyclic ring;
R₃ to R₆ are identical or different and represent hydrogen, hydroxyl, halogen, C₁–C₆-alkyl, C₅–C₇-cycloalkyl, phenyl which is optionally substituted by C₁–C₄-alkyl, halogen, and/or C₁–C₄-alkoxy, C₇–C₉-aralkyl, whose aryl radical is optionally substituted by C₁–C₄-alkyl, halogen and/or C₁–C₄-alkoxy, or C₁–C₄-alkoxy,
R₇, R₈, R₉, R₁₀ and R₁₁ are identical or different and represent hydrogen or C₁–C₆-alkyl,
X represents a single bond or methylene which is optionally monosubstituted or disubstituted by C₁–C₄-alkyl, oxygen or —NR₁₇,
wherein $R_{17}$ represents hydrogen or $C_1$–$C_4$-alkyl or $R_{17}$ together with $R_7$ forms a $C_2$-alkylene ring-closing member and $R_{12}$, $R_{13}$, $R_{14}$, $R_{15}$ and $R_{16}$ are identical or different and represent hydrogen, hydroxyl, halogen, $C_1$–$C_6$-alkyl, $C_5$- or $C_6$-cycloalkyl, benzyl, $C_1$–$C_4$-alkoxy, trifluoromethyl, or $R_{12}$ and $R_{13}$ or $R_{13}$ and $R_{14}$ together form a $C_1$–$C_3$-alkylenedioxy group or a —CH=CH—CH=CH— group, and their pharmaceutically acceptable acid addition salts.

2. A compound according to formula (I) in claim 1, in which $R_1$ and $R_2$, are identical or different, and represent hydrogen or $C_1$–$C_4$-alkyl or together with the carbon atom which joins them represent a carbocyclic $C_5$- or $C_6$-ring, $R_3$ to $R_6$, are identical or different, and denote hydrogen, hydroxyl, $C_1$–$C_4$-alkyl, $C_1$–$C_4$-alkoxy or chlorine, $R_7$ to $R_{11}$, are identical or different, and represent hydrogen or $C_1$–$C_4$-alkyl, X represents a single bond, oxygen, methylene or —$NR_{17}$, wherein $R_{17}$ denotes hydrogen or $C_1$–$C_3$-alkyl or $R_{17}$ together with $R_7$ forms an ethylene ring-closing member and $R_{12}$ to $R_{16}$, are identical or different, and denote hydrogen, chlorine, cyclohexyl, $C_1$–$C_4$-alkyl, $C_1$–$C_3$-alkoxy or trifluoromethyl, or $R_{12}$ and $R_{13}$ or $R_{13}$ and $R_{14}$ together form a methylenedioxy group or —CH=CH—CH=CH—.

3. A compound of claim 1 which is 4-[γ-(3,4-Methylenedioxyphenyl)-α-methyl]-propyl-amino-methyl-2-spirocyclopentachroman.

4. A compound of claim 1 which is 4-(β-Phenylethyl)-aminomethyl-2-spirocyclopentachroman.

5. A compound of claim 1 which is 4-N-3,4-Dichlorophenylpiperazin-N'-yl-methyl-2,2-dimethyl-chromene.

6. A compound of claim 1 which is 4-β-Phenoxyethyl-aminomethyl-2-spirocyclopenta-chroman.

7. A compound of claim 1 which is 4-[γ-(2,3,4-trimethoxyphenyl)-α-methyl]-propylamino-methyl-2-spirocyclopentachoman.

8. A compound of claim 1 which is 4-[γ-(3,4-methylenedioxyphenyl)-α-methyl]propylamino-methyl-7-methoxy-2-spirocyclopentachroman.

9. A compound of claim 1 which is 4-[γ-(3,4-methylenedioxyphenyl)-α-methyl]propylamino-methyl-7-methyl-2-spirocyclopentachroman.

10. A compound of claim 1 which is 4-[γ-(2-trifluoromethyl)-α-methyl]propylamino-methyl-2-spirocyclopentachroman.

11. A pharmaceutical composition containing as an active ingredient an amount effective for combating circulatory illness of a compound according to claim 1 together with an inert pharmaceutical carrier.

12. A pharmaceutical composition containing as an active ingredient an amount effective for combating circulatory illness of a compound of claim 1 in the form of a sterile or physiologically isotonic aqueous solution.

13. A composition according to claim 11 containing from 0.5 to 90% by weight of said active ingredient.

14. A medicament in dosage unit form comprising an amount effective for combating circulatory illness of a compound according to claim 1 and an inert pharmaceutical carrier.

15. A medicament of claim 14 in the form of a tablet, pill, dragee, capsule, ampoul or suppository.

16. A method for combating circulatory illness in warm-blooded animals which comprises administering to said animals an amount effective for combating circulatory illness of an active compound according to claim 1 either alone, or in admixture with a diluent or in the form of a medicament.

17. A method according to claim 16 in which the active compound is administered in an amount of 0.001 to 10 mg per kg body weight per day intravenously.

18. A method according to claim 16 in which the active compound is administered in an amount of 0.5 to 30 mg per kg body weight per day orally.

* * * * *